(12) United States Patent
Elmaleh et al.

(10) Patent No.: US 11,491,288 B2
(45) Date of Patent: Nov. 8, 2022

(54) DISPENSER FOR DRY-POWDER INHALATION DEVICES

(71) Applicants: Seroton, Inc., Boston, MA (US); THE GENERAL HOSPITAL CORPORATION, Boston, MA (US)

(72) Inventors: David R. Elmaleh, Newton, MA (US); Maxim D. Elmaleh, Newton, MA (US)

(73) Assignees: SEROTON, INC.; THE GENERAL HOSPITAL CORPORATION

( * ) Notice: Subject to any disclaimer, the term of this patent is extended or adjusted under 35 U.S.C. 154(b) by 677 days.

(21) Appl. No.: 16/384,670

(22) Filed: Apr. 15, 2019

(65) Prior Publication Data
US 2019/0321571 A1 Oct. 24, 2019

Related U.S. Application Data

(63) Continuation-in-part of application No. 14/518,487, filed on Oct. 20, 2014, now Pat. No. 10,258,751.
(Continued)

(51) Int. Cl.
*A61M 15/00* (2006.01)
*A61M 16/14* (2006.01)

(52) U.S. Cl.
CPC .... *A61M 15/0063* (2014.02); *A61M 15/0035* (2014.02); *A61M 15/0041* (2014.02);
(Continued)

(58) Field of Classification Search
CPC .. A61M 15/0028; A61M 15/004–0041; A61M 11/003; A61M 15/0035;
(Continued)

(56) References Cited

U.S. PATENT DOCUMENTS

| 3,991,761 A | 11/1976 | Cocozza |
| 7,077,130 B2 | 7/2006 | Nichols et al. |

(Continued)

FOREIGN PATENT DOCUMENTS

| EP | 0 385 156 B1 | 9/1990 |
| EP | 0 558 879 B1 | 9/1993 |

(Continued)

OTHER PUBLICATIONS

International Search Report of PCT Application No. PCT/US2020/028117, dated Jul. 1, 2020.
(Continued)

*Primary Examiner* — Elliot S Ruddie
(74) *Attorney, Agent, or Firm* — Pearl Cohen Zedek Latzer Baratz LLP

(57) ABSTRACT

A dispenser for dispensing one or more dry-powder inhaler devices, having at least one compartment configured to hold at least one dry-powder inhaler device, the at least one dry-powder inhaler device comprising a casing enclosing at least one compartment containing an inhalable medicament covered by a cover, and at least one puncture mechanism comprising at least one pin structure operably aligned with the at least one compartment, and at least one obstruction internally located within the dispenser and adjacent to an opening, wherein, upon a dry-powder inhaler device being pulled from a dispenser, the at least one obstruction is configured to actuate the at least one puncture mechanism to extend the at least one pin structure into the casing, thereby puncturing the cover of the at least one compartment.

18 Claims, 20 Drawing Sheets

Related U.S. Application Data which is a continuation-in-part of application No. 14/150,268, filed on Jan. 8, 2014, now Pat. No. 10,238,820.

(52) U.S. Cl.
CPC ....... *A61M 16/14* (2013.01); *A61M 2202/064* (2013.01); *A61M 2205/0216* (2013.01); *A61M 2209/06* (2013.01)

(58) Field of Classification Search
CPC .......... A61M 11/0031; A61M 11/0033; A61M 11/0035; A61M 15/0003; A61M 15/0008; A61M 15/0091; A61M 15/0093; A61M 15/06; A61M 15/0061–0063; A61M 16/14; A61M 2202/064; A61M 2205/0216; A61M 2205/276; A61M 2209/06
USPC .................................................. 128/203.15
See application file for complete search history.

(56) References Cited

U.S. PATENT DOCUMENTS

| | | |
|---|---|---|
| 9,283,336 B2 | 3/2016 | Jones et al. |
| 10,010,687 B2 | 7/2018 | Von Schuckmann |
| 2001/0007853 A1 | 7/2001 | Dimarchi et al. |
| 2001/0053761 A1 | 12/2001 | Dimarchi et al. |
| 2004/0154618 A1 | 8/2004 | Edwards et al. |
| 2007/0283955 A1 | 12/2007 | Tsutsui |
| 2010/0051023 A1 | 3/2010 | Kladders |
| 2011/0220106 A1 | 9/2011 | Ganem et al. |
| 2013/0042864 A1 | 2/2013 | Adler et al. |
| 2013/0061851 A1 | 3/2013 | Jones et al. |
| 2014/0150787 A1 | 6/2014 | Ellwanger et al. |
| 2015/0190595 A1 | 7/2015 | Elmaleh et al. |

FOREIGN PATENT DOCUMENTS

| | | |
|---|---|---|
| EP | 0 629 136 B1 | 12/1994 |
| EP | 0 973 570 B1 | 1/2000 |
| WO | WO 92/004069 A1 | 3/1992 |
| WO | WO 93/017728 A1 | 9/1993 |
| WO | WO 98/034663 | 8/1998 |
| WO | WO 02/055142 A2 | 7/2002 |
| WO | WO 08/124666 A2 | 10/2008 |
| WO | WO 2011/080747 A2 | 7/2011 |
| WO | WO 2014/006135 A2 | 1/2014 |

OTHER PUBLICATIONS

Wolff et al., "Generation of Aerosolized Drugs", J. Aerosol. Med. pp. 89-106 (1994).

Wagenseil, L.et al., "Optimization and performance of the resQhaler—a single-use disposable dry powder inhaler", Drug Delivery to the Lungs 22, Christian-Albrechts-Universitat zu Kiel, Edinburgh, Scotland, 2011.

Aespira Investor Presentation, "Breathing new life in healthcare", 2013.

International Search Report for International Application No. PCT/US2015/010506, dated May 1, 2015.

Office Action for U.S. Appl. No. 14/150,268, dated Mar. 7, 2016.

Search Report of European Application No. EP 15 73 5379, dated Jun. 28, 2017.

Office Action of Japanese Application No. JP2016-545994 dated Nov. 27, 2018.

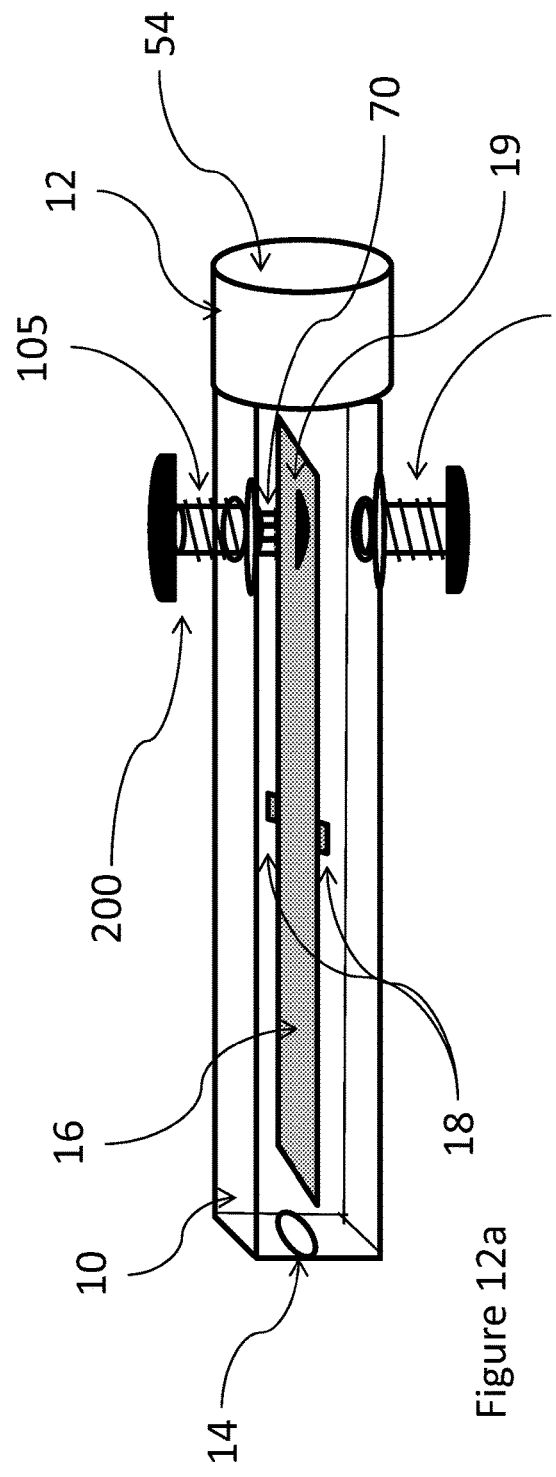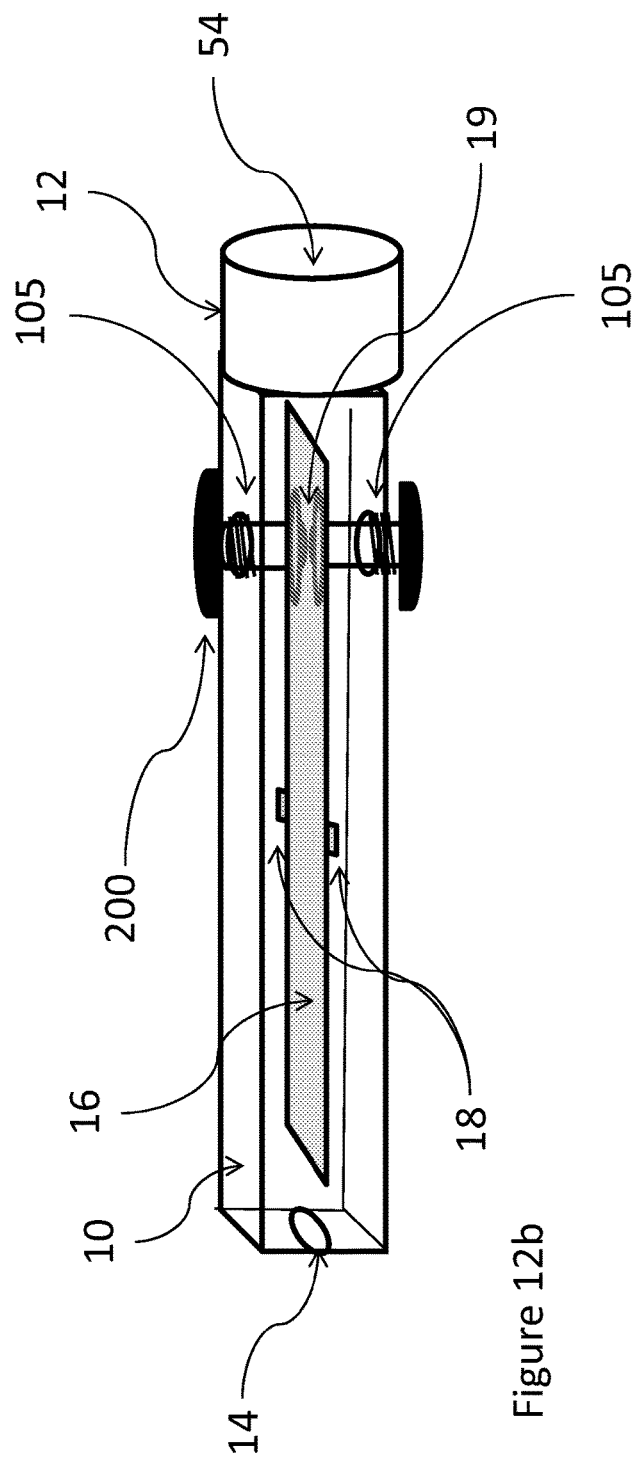
Figure 12a
Figure 12b

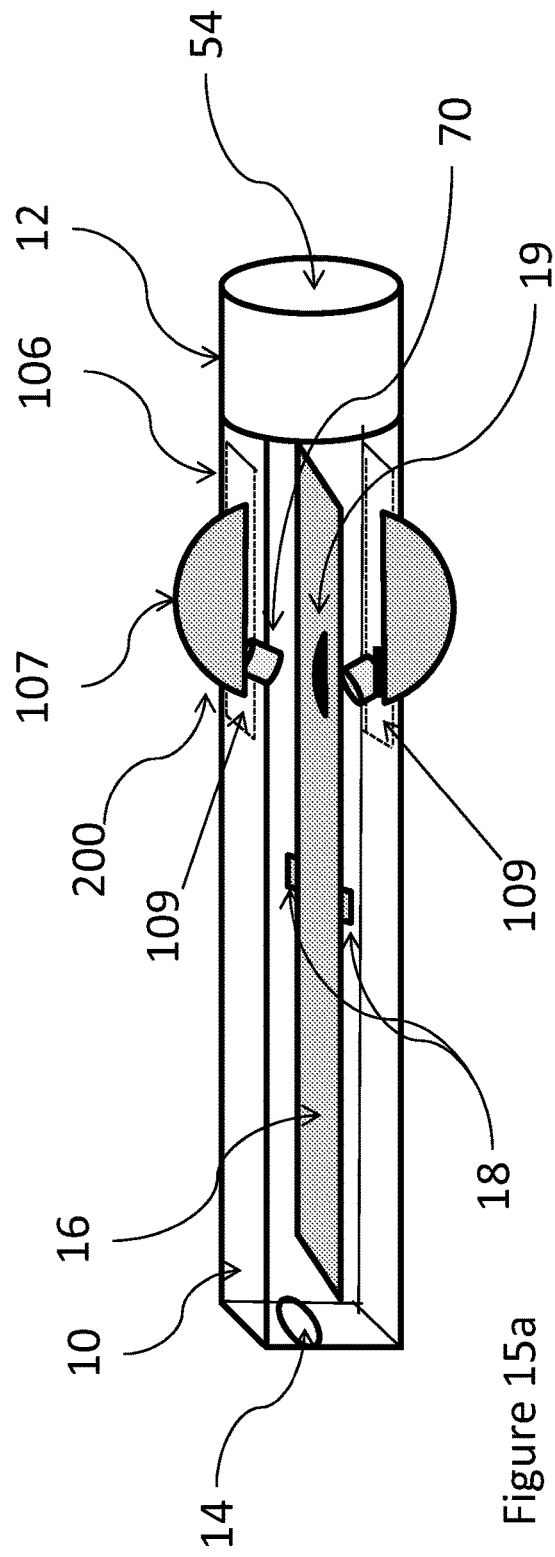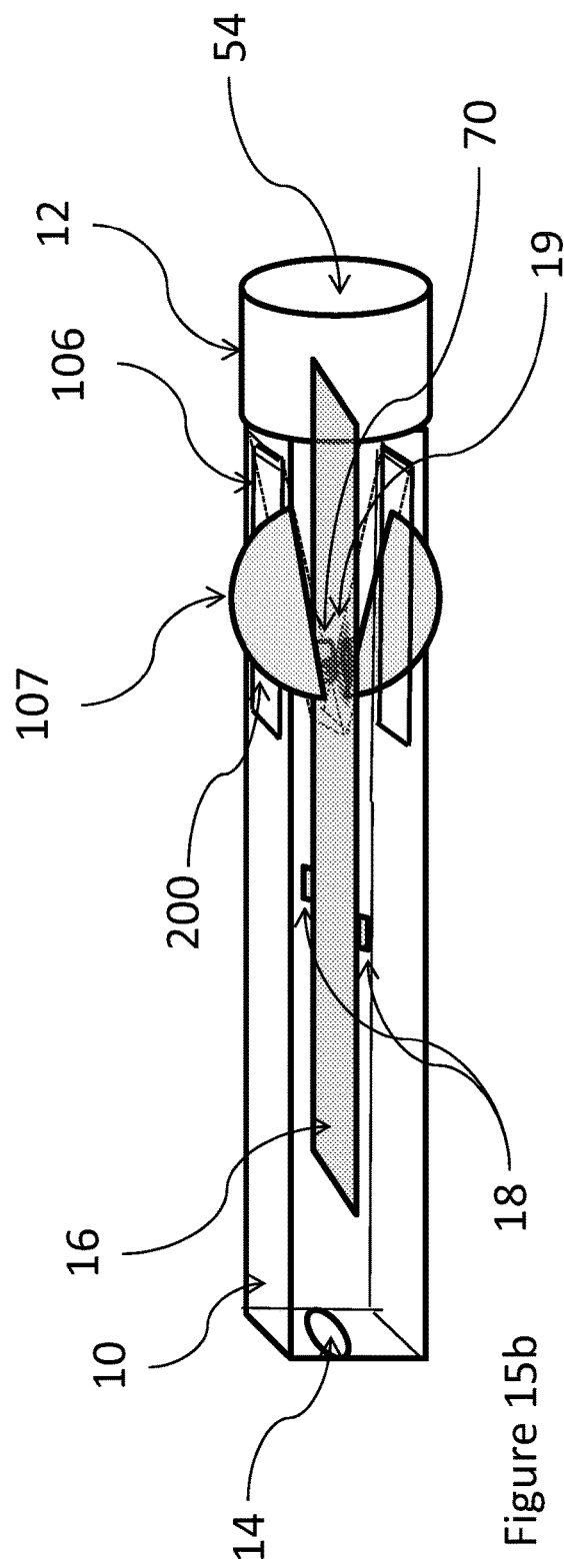
Figure 15a
Figure 15b

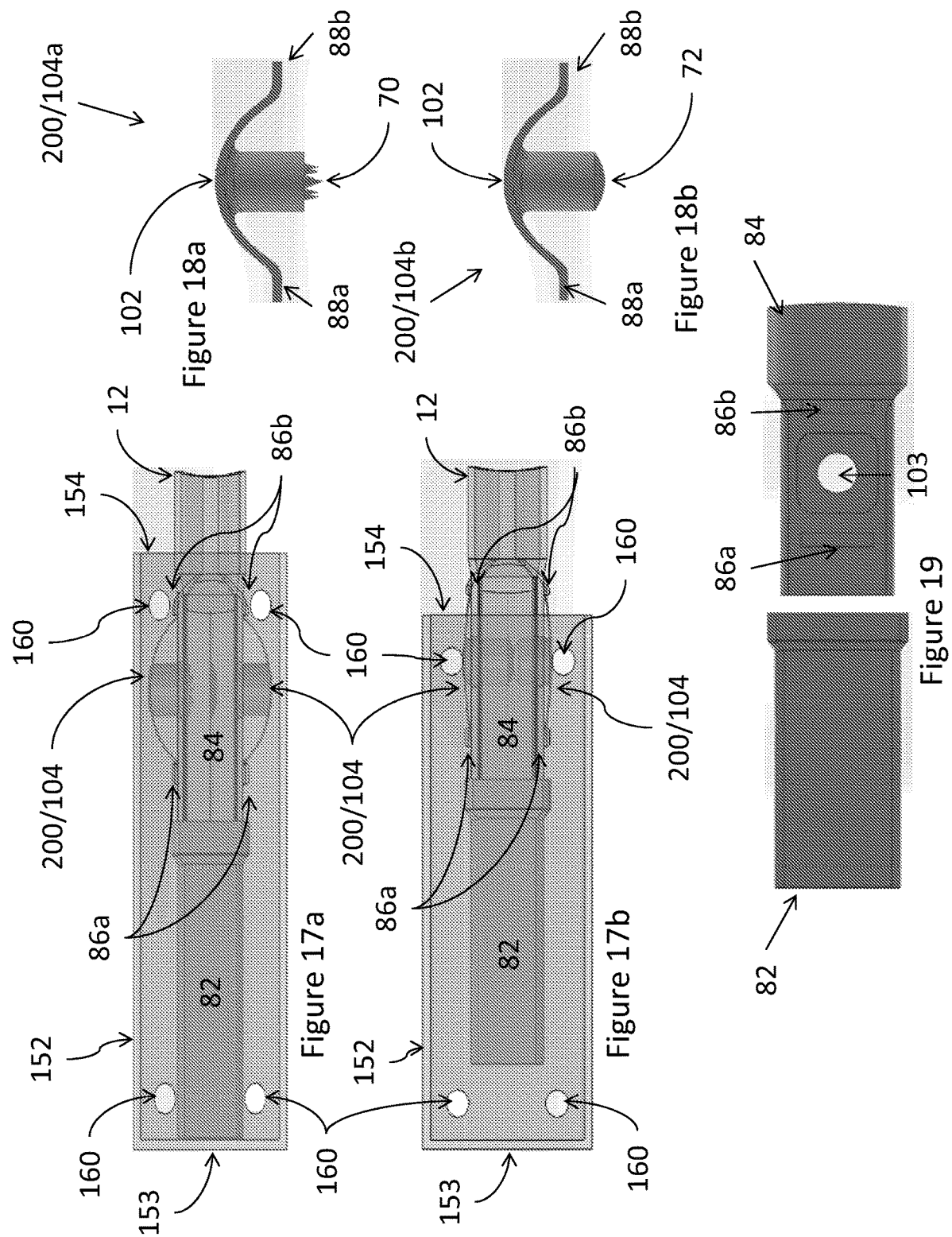

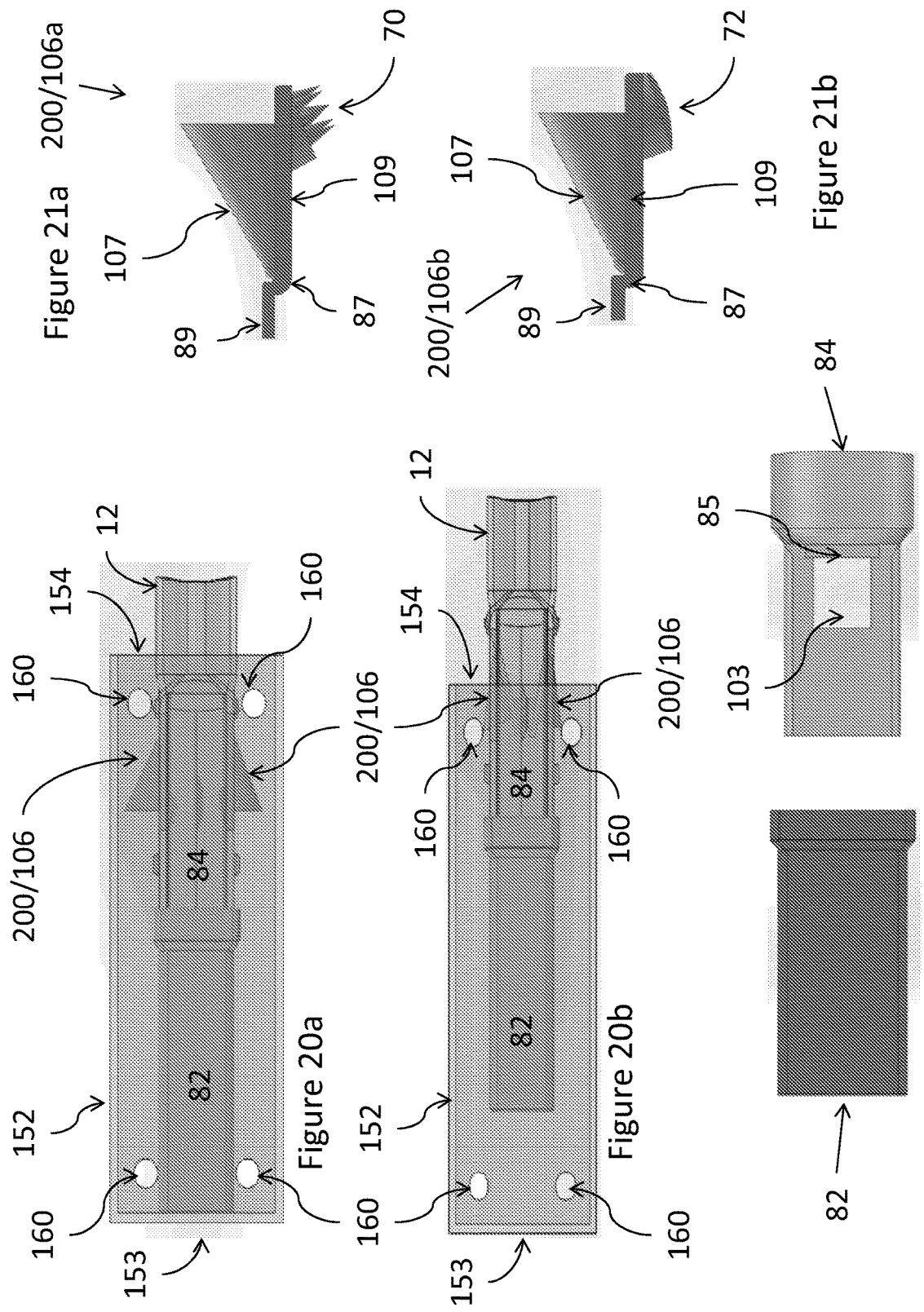

DISPENSER FOR DRY-POWDER INHALATION DEVICES

CROSS-REFERENCE TO RELATED APPLICATIONS

This application is a continuation-in-part of U.S. patent application Ser. No. 14/518,487, filed Oct. 20, 2014, now U.S. Pat. No. 10,258,751, issued Apr. 16, 2019, which is a continuation-in-part of U.S. patent application Ser. No. 14/150,268, filed Jan. 8, 2014, now U.S. Pat. No. 10,238,820, issued Mar. 26, 2019, each of which is hereby incorporated by reference in its entirety.

FIELD OF THE INVENTION

The present invention relates to improvements to dry-powder inhalers for the treatment of respiratory diseases and systemic drug delivery via deep lung access, and a kit for dispensing the dry-powder inhalers.

BACKGROUND OF THE INVENTION

Numerous drugs, medications and other substances are inhaled into the lungs for rapid absorption in the blood stream and systemic delivery, or alternatively for therapeutic treatment locally. Inhaled drugs are typically either in aerosolized or powder form. In either case, the delivered agent should have a particle or droplet nuclei size that is 5 microns or less in order to reach the terminal ramifications of the respiratory tree.

Such small particles are, however, thermodynamically unstable due to their high surface area to volume ratio, which provides significant excess surface free energy and encourages particles to agglomerate. Agglomeration of the particles, and adherence of the particles to the internal surfaces of the inhaler, result in delivery of particles that are too large in size, delivery of a lower dose due to particles adhering to the interior surfaces of the inhaler, and poor flow and non-uniform dispersion resulting in the delivery of a varying dosage. In addition, as noted above, many dry-powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, the hygroscopic nature of many dry-powder drugs may also require that the device be cleansed (and dried) at periodic intervals.

U.S. Patent Application Publication No. 2013/0042864, filed Oct. 3, 2012, which is hereby incorporated herein by reference in its entirety, describes a dry-powder inhaler including a casing having an air inlet located at a first terminus, a powder delivery port located at a second terminus and positioned distal to the air inlet, and an elongated assembly located within the interior of the casing. A first assembly terminus is located proximally to the air inlet, and a second assembly terminus is located proximally to the powder delivery port. The elongated assembly is fitted within the casing such that the assembly partially rotates within the casing about a single axis, and said elongated assembly comprises at least one compartment containing a dry-powder and located proximally to the second assembly terminus. The dry-powder compartment includes a porous structure encasing the dry-powder; whereby airflow through the device causes the assembly to partially rotate or pivot within the casing about a single axis, and dry-powder is thereby released from the compartment and becomes entrained in the airflow.

However, it is important to provide a single use (disposable) dry-powder inhalation device that facilitates the dispersion of active drug powder and delivers a consistent dose to the lung for respiratory disease treatment or the deep lung for systemic drug delivery. Many inhalation devices, such as described in U.S. Patent Application Publication No. 2013/0042864, require a mesh to be arranged over the dry-powder compartment and an additional film to be placed over the mesh in order to hermetically seal the compartment from air and prevent loss of the drug by movement or transport. Unfortunately, the process of filling the compartment, placing the mesh over the compartment and placing the film over the mesh is expensive and slow. Furthermore, the film is attached by glue or press, and must be pulled from over the cavity before use. However, pulling the film will twist the thin elongated assembly and disrupt its delicate rotating operation. Furthermore, developing an appropriate removable system and assembling it as an integrated part of the inhalation device is expensive and will require careful, complicated operating instructions.

Therefore, a need exists for improved disposable, single dose, dry-powder inhalation device that facilitates the dispersion of active drug powder and delivers a consistent dose to the lung, and that does not utilize mesh, cover film, glue or other means to seal the dry powder compartment.

In addition, a need exists for an improved single dose disposable dry-powder inhalation device that facilitates the dispersion of active drug powder and delivers a consistent dose to the lung the inhaler, but that does not require pushing, pulling or twisting of the inhalation device or of any of its components in order to withdraw the active drug powder from the dry-powder compartment.

SUMMARY OF THE INVENTION

Accordingly, it is the object of the present invention to provide an improved dry-powder inhalation device which obviates the need to use a mesh and film to cover the dry-powder compartment. Without the mesh and the film, the improved dry-powder inhaler has a greatly reduced cost of packaging and assembly, as well as, cost of operation and development.

It is an object of the present invention to provide an improved dry-powder inhalation device in which the dry-powder compartment is covered with a simple blister-type cover that protects the drug from moisture and light. Such blister-type covers may be composed of a thin but durable material that protects the drug in the compartment from moisture and light and may be easily punctured or ruptured, for example, aluminum, aluminum foil, plastic, or a cellophane-like material, e.g., made of regenerated cellulose, or other suitable material.

It is another object of the present invention to simplify the assembly of typical dry-powder inhalation devices, such that filling of the dry-powder compartment with the active drug powder and covering/sealing of the filled dry-powder compartment can be done inexpensively and quickly, while still being done hermetically.

It is a further object of the present invention to simplify the withdrawal of the active drug powder from the dry-powder compartment by eliminating the need for a mesh and a mesh cover, as in the above-mentioned dry-powder inhalation devices. The uncovering or opening of the herein described dry-powder compartment and withdrawal of the active drug powder does not cause twisting or pulling and improper operation of the inhaler.

In accordance with these and other objects of the invention, the invention relates to a dry-powder inhalation device whose dry-powder compartment is covered with a puncturable covering, such as thin aluminum foil, cellophane or other known blister-pack type coverings, and sealed as known in the art. In addition, a region on an interior portion of the casing includes one or more fins, pins, edges, or other type of sharp or pointed needle- or pin-like structures. This region is arranged over or proximal to, and in alignment with, the puncturable covering of the dry-powder compartment, and is arranged such that, when the user inhales, the pin-like structures puncture the covering of the dry-powder compartment, causing the dry-powder compartment to be opened and the active drug powder within it to be withdrawn therefrom for inhalation by the user.

The punctured compartment produces the same effect as does a mesh used in the prior art, i.e., providing the powder dry powder on demand. It is important to note that, in contrast to the prior art mesh and sealant, in which the inhaler film must be resistant to moisture, the arrangement of the present invention protects the air inlet and outlet opening from air and moisture. In other embodiments, a removable film may be added in order to maintain the inhaler's sterile conditions.

For example, the invention can be adapted for use with known dry-powder inhalation devices, such as disclosed in US Patent Application Publication No. 2013/0042864, by placing such pin-like structures at the upper or lower surface of the casing and placing the covered dry-powder compartment on the elongated support panel that rotates within the casing. When the elongated support panel rotates towards the top surface of the casing, the covered dry-powder compartment is forced against the pin-like structures. Once the puncturable covering of the dry-powder compartment at the end of the elongated support panel strikes against the pin-like structures at the upper or lower surface of the casing, the needle- or pin-like structures puncture the puncturable covering the dry-powder compartment, thereby releasing the dry-powder from the compartment.

Alternatively, the invention can be adapted for use with known dry-powder inhalation devices, such as disclosed in US Patent Application Publication No. 2013/0042864, in an alternative manner, by placing such pin-like structures on the top or bottom surface of the elongated support panel that rotates within the casing and at the end thereof. When the elongated support panel rotates towards the top or bottom surface of the casing, it strikes the covering of the dry-powder filled compartment that is situated on the upper or lower surface of the casing. Once the pin-like structures at the end of the elongated support panel strike the puncturable covering, the needle- or pin-like structures puncture the puncturable covering the dry-powder compartment, thereby releasing the dry-powder from the compartment.

In certain embodiments of the present invention, the cover of the drug compartment is punctured just prior to inhalation by the user pressing a retractable button, which allows the needle- or pin-like structures to be extended and then retracted. The retraction of the arrangement of the needle- or pin-like structures avoids potential vibration interference, i.e., where the needles or pins stay at the same extended position and continue to touch the drug compartment cover with each vibration of the elongated support panel.

In certain embodiments, the arrangement provides a drug compartment on only the upper or lower side of the elongated support panel, while the other side is not punctured and simply supports holding the drug compartment to be punctured. That is, the platform is rigid on the opposing side of the drug compartment and may not be punctured. In some embodiments, the pins may be on the side of the elongated support panel having the drug compartment.

Modern improved inhalation devices use multi-dose blisters for drug delivery, mainly for diseases associated with the respiratory system. Some advantages of these inhalation devices are delivery of dose consistency and compliance. Some inhalation devices, such as those from MicroDose Therapeutx, Inc., claim potential control of exhaling into the device, piezo-electric mechanism for efficient delivery, and counting and protecting the user from taking repeated dose. However, the complexity of these devices and their validation is costly, and these devices are still not fool-proof delivery systems. In addition, the delivered drug amount is limited.

The single disposable inhaler described herein allows those controls without the requirement of a complex electric and/or chip to be developed for the drug. A simple package arrangement and day printing on the container does the trick. The production costs are low. Following its use, the patient can dispose of the inhaler. No cleaning or resting and cartridge refilling of the device is required.

BRIEF DESCRIPTION OF THE DRAWINGS

The subject matter regarded as the invention is particularly pointed out and distinctly claimed in the concluding portion of this specification. The invention, however, both as to organization and method of operation, together with objects, features, and advantages thereof, may best be understood by reference to the following detailed descriptions when read with the accompanying drawings in which:

FIGS. 12a and 12b show perspective views of a push button having a coiled spring mechanism according to certain embodiments of the present invention;

FIGS. 15a and 15b are perspective views of a push button having a living hinge according to certain aspects of the present invention;

FIG. 16 modification of a rectangular box to a sleeve cover as a separate single inhaler for single dose dispensing as an alternative to the multi dose carrier in FIG. 16.

FIGS. 17a and 17b show schematic views of a dispenser having a leaf-spring mechanism for use in dispensing a dry-powder inhaler device according to certain embodiments of the present invention;

FIGS. 18a and 18b show side views of a push button, integrated leaf-spring or nail type mechanism according to certain embodiments of the present invention;

FIG. 19 shows an exploded view of a two-piece casing of a dry-powder inhaler device and dispenser according to certain aspects of the present invention;

FIGS. 20a and 20b show schematic views of a dispenser having a living hinge for use in dispensing a dry-powder inhaler device according to certain embodiments of the present invention;

FIGS. 21a and 21b show side views of a push button, living leaf assembly and living hinge assembly respectively according to certain embodiments of the present invention;

FIG. 22 shows an exploded view of a two-piece casing of a dry-powder inhaler device and dispenser according to certain aspects of the present invention.

Figure 1:
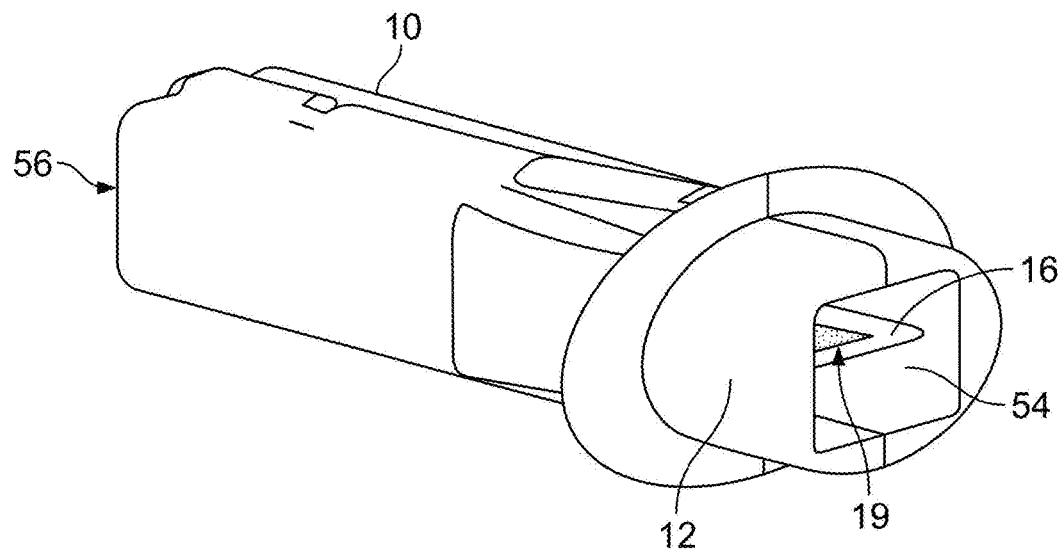
FIG. 1 shows a perspective view of a first embodiment of the inhalation device.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components have not been described in detail so as not to obscure the present invention.

This invention, inter alia, takes advantage of flow energy of inspired air to disperse neat or formulated micronized particles packaged in a dosage form. The present invention provides a novel inhaler device, in which a principle mode of operation of the device is the production of a beating action within the device, which facilitates, or causes, the release of a dry-powder drug contained in a blistered compartment located within the device.

The devices, kits and/or methods of the present invention may be particularly suitable to dispense dry-powder substances to in-vivo subjects, including animal and, typically, human subjects. The dry-powder substance may include one or more active pharmaceutical constituents as well as biocompatible additives that form the desired formulation or blend.

As used herein, the term "dry-powder" is used interchangeably with "dry-powder formulation" and means the dry-powder can comprise one or a plurality of constituents or ingredients with one or a plurality of (average) particulate size ranges.

In some embodiments, individual dispensable quantities of dry-powder formulations can be a single ingredient or a plurality of ingredients, whether active or inactive. The inactive ingredients can include additives added to enhance flowability or to facilitate aerosolization delivery to the desired systemic target. The dry-powder drug formulations can include active particulate sizes that vary.

In some embodiments, the dry-powder may comprise any therapeutic agent such as, for example, a drug or vaccine.

In some embodiments, any drug or drugs that may be administered by inhalation and that are either a solid or may be incorporated in a solid carrier are envisioned for incorporation within the inhalers, kits and/or methods of this invention. In some embodiments, the drug will be a drug for the treatment of a respiratory disease or condition. In some embodiments, such drugs may comprise bronchodilators, corticosteroids and drugs for the prophylaxis of asthma. Other drugs such as anorectics, anti-depressants, anti-hypertensive agents, anti-neoplastic agents, anti-cholinergic agents, dopaminergic agents, amyloid plaque treatment, protein and prion protein mis-folding, neurodegeneration, narcotic analgesics, beta-adrenergic blocking agents, pro stoglandins, sympathomimetics, tranquilizers, steroids, vitamins and/or hormones may be employed. Exemplary drugs include: Salbutamol, Terbutaline, Rimiterol, Fentanyl, Fenoterol, Pirbuterol, Reproterol, Adrenaline, Isoprenaline, Ociprenaline, Ipratropium, Beclomethasone, Betamethasone, Budesonide, Disodium Cromoglycate and analogs, Nedocromil Sodium, Ergotamine, Salmeterol, Fluticasone, Formoterol, Insulin, Atropine, Prednisolone, Benzphetamine, Chlorphentermine, Amitriptyline, Imipramine, Cloridine, Actinomycin C, Bromocriptine, Buprenorphine, Propranolol, Lacicortone, Hydrocortisone, Fluocinolone, Triamcinclone, Dinoprost, Xylometazoline, Diazepam, Lorazepam, Folic acid, Nicotinamide, Clenbuterol, Bitolterol, Ethinyloestradiol and Levenorgestrel. Drugs may be formulated as a free base, one or more pharmaceutically acceptable salts or a mixture thereof.

The dry-powder formulation can also include desired excipients. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

Examples of diseases, conditions or disorders that may be treated or prevented with the inhalers, kits and/or methods of the invention include, but are not limited to, asthma, COPD (chronic obstructive pulmonary disease), viral or bacterial infections, influenza, allergies, and other respiratory ailments, as well as, diabetes, other related insulin resistance disorders and neurodegeneration. The dry-powder inhalant administration may be used to deliver locally acting agents such as antimicrobials, protease inhibitors, and nucleic acids/oligonucleotides as well as systemic agents such as peptides like leuprolide and proteins such as insulin.

For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., Generation of Aerosolized Drugs, J. Aerosol. Med. pp. 89-106 (1994). See also U.S. Patent Application Publication No. 2001/0053761, entitled "Method for Administering ASPB28-Human Insulin", and U.S. Patent Application Publication No. 2001/0007853, entitled "Method for Administering Monomeric Insulin Analogs", the contents of which are hereby incorporated herein by reference in their entirety.

Typical dose amounts of the unitized dry-powder mixture dispersed in the inhaler will vary depending on the patient size, the systemic target, and the particular drug. Typical doses that can be delivered by the inhaler range from 10 μg to 10 mg. Some additional exemplary dry-powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry-powder formulations may be configured as a smaller administrable dose compared to the conventional doses. For example, each administrable dry-powder dose may be on the order of less than about 60-70% of that of conventional doses. In certain particular embodiments, using the active dispersal systems provided by certain embodiments of the dry-powder inhaler configurations of the instant invention, the adult dose may be reduced to under about 15 mg, such as between about 10 μg to 10 mg. The active constituent(s) concentration may be between about 5-10%. In other embodiments, active constituent concentrations can be in the range of between about 10-20%, 20-25%, or even larger, up to the case where only pure drug is delivered.

In certain particular embodiments, during dose dispensing, the dry-powder in a particular dose receptacle may be formulated as an active pharmaceutical constituent(s) substantially without additives (such as excipients). As used herein, "substantially without additives" means that the dry-powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry-powder formulation, and, in certain embodiments, the non-active ingredients are present in only trace amounts.

In some embodiments, the therapeutic agent can be a biologic, which includes, but is not limited to, proteins, polypeptides, carbohydrates, polynucleotides, and nucleic acids. In some embodiments, the protein can be an antibody, which can be polyclonal or monoclonal. In some embodiments, the therapeutic can be a low molecular weight molecule. In addition, the therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, antacids, anti-diarrheals, antidotes, anti-folics, antipyretics, anti-rheumatic agents, psychotherapeutic agents, neural blocking agents, anti-inflammatory agents, drugs that treat diseases associated with amyloidosis and peptide and protein mis-folding, such as prion (mad cow disease), Alzheimer's and Parkinson's diseases, anti-helmintics, anti-arrhythmic agents, antibiotics, anticoagulants, antidepressants, anti-diabetic agents, anti-epileptics, antifungals, antihistamines, antihypertensive agents, anti-muscarinic agents, anti-mycobacterial agents, anti-malarials, antiseptics, antineoplastic agents, antiprotozoal agents, immunosuppressants, immunostimulants, antithyroid agents, antiviral agents, anxiolytic sedatives, bone and skeleton agents, astringents, beta-adrenoceptor blocking agents, cardiovascular agents, chemotherapy agents, corticosteroids, cough suppressants, diagnostic agents, diagnostic imaging agents, diuretics, dopaminergics, enzymes and enzyme cofactors, gastrointestinal agents, growth factors, hematopoietic or thrombopoietic factors, hemostatics, hematological agents, hemoglobin modifiers, hormones, hypnotics, immunological agents, anti-hyperlipidemic and other lipid regulating agents, muscarinics, muscle relaxants, parasympathomimetics, parathyroid hormone, calcitonin, prostaglandins, radio pharmaceuticals, sedatives, sex hormones, anti-allergic agents, stimulants, steroids, sympathomimetics, thyroid agents, therapeutic factors acting on bone and skeleton, vasodilators, vaccines, vitamins, and xanthines. Anti-neoplastic, or anti-cancer agents, include but are not limited to, paclitaxel and derivative compounds, and other anti-neoplastics selected from the group consisting of alkaloids, anti-metabolites, enzyme inhibitors, alkylating agents and antibiotics.

Exemplary proteins, include therapeutic proteins or peptides, or carrier proteins or peptides, including GCSF, GMCSF, LHRH, VEGF, hGH, lysozyme, alpha-lactoglobulin, basic fibroblast growth factor (bFGF), asparaginase, tPA, urokin-VEGF, chymotrypsin, trypsin, streptokinase, interferon, carbonic anhydrase, ovalbumin, glucagon, ACTH, oxytocin, phosphorylase b, secretin, vasopressin, levothyroxine, phatase, beta-galactosidase, parathyroid hormone, calcitonin, fibrinogen, polyaminoacids (e.g., DNAse, alphal antitrypsin, polylysine, polyarginine), angiogenesis inhibitors or pro-immunoglobulins (e.g., antibodies), somatostatin and analogs thereof, casein, collagen, soy protein, and cytokines (e.g., interferon, interleukin and others), immunoglobulins, Exemplary hormones and hormone modulators include proinsulin, C-peptide of insulin, a mixture of insulin and C-peptide of insulin, hybrid insulin cocrystals, growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, steroids, estradiols, dexamethazone, testosterone, and other factors acting on the genital organs and their derivatives, analogs and congeners.

Exemplary hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation, thrombopoietin, platelet proliferation stimulating factor, megakaryocyte proliferation (stimulating) factor, and factor VIII.

Exemplary therapeutic factors acting on bone and skeleton and agents for treating osteoporosis include calcium, alendronate, bone GLa peptide, parathyroid hormone and its active fragments, histone H4-related bone formation and proliferation peptide and their muteins, derivatives and analogs thereof.

Exemplary enzymes and enzyme cofactors include: pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD).

Exemplary vaccines include Hepatitis B, Influenza, MMR (measles, mumps, and rubella), and Polio vaccines and others.

Exemplary growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and so on.

Exemplary agents acting on the cardiovascular system include factors that control blood pressure, arteriosclerosis, etc., such as endothelins, endothelin inhibitors, endothelin antagonists, endothelin producing enzyme inhibitors vasopressin, renin, angiotensin I, angiotensin II, angiotensin III, angiotensin I inhibitor, angiotensin II receptor antagonist, atrial naturiuretic peptide (ANP), antiarrythmic peptide and so on.

Exemplary factors acting on the central and peripheral nervous systems include opioid peptides (e.g. enkephalins, endorphins), neurotropic factor (NTF), calcitonin gene-related peptide (CGRP), thyroid hormone releasing hormone (TRH), salts and derivatives of TRH, neurotensin and so on.

Exemplary chemotherapeutic agents, such as paclitaxel, mytomycin C, BCNU, and doxorubicin.

Exemplary agents acting on the respiratory system include factors associated with asthmatic responses, e.g., albuterol, fluticazone, ipratropium bromide, beclamethasone, and other beta-agonists and steroids.

Exemplary steroids include, but are not limited to, beclomethasone (including beclomethasone dipropionate), fluticasone (including fluticasone propionate), budesonide, estradiol, fludrocortisone, flucinonide, triamcinolone (including triamcinolone acetonide), and flunisolide. Exemplary beta-agonists include, but are not limited to, salmeterol xinafoate, formoterol fumarate, levo-albuterol, bambuterol, and tulobuterol.

Exemplary anti-fungal agents include, but are not limited to, itraconazole, fluconazole, and amphotericin B.

Numerous combinations of active agents may be desired including, for example, a combination of a steroid and a beta-agonist, e.g., fluticasone propionate and salmeterol, budesonide and formoterol, etc.

The inhalers of this invention are dry-powder inhaler devices, comprising a casing, such as, for example, a rectangular or tubular shaped box or enclosure. In certain embodiments, the casing includes an elongated longitudinal axis, and includes a first terminus and a second terminus opposite the first terminus. The casing further includes an air inlet located at the first terminus of the casing and a powder delivery port located at the second terminus of the casing, said powder delivery port being located distal to the air inlet.

The term "casing" refers to, inter alia, the container comprising the various elements of the device as described herein. The casing may be of any appropriate material, including, in some embodiments, any plastic or other appropriate synthetic material, which may be prepared to conform to the desired structure and will contain or comprise the elements described herein. In some embodiments, the casing may comprise a Polycarbonate or HDPE.

The casing will include two openings placed at opposite ends of the casing. One such opening is the air inlet, which inlet is sufficient in size to facilitate air entry and exit therefrom. Another opening in the casing is a powder delivery port, which powder delivery port is positioned at an opposite end of the casing from that of the air inlet.

The powder delivery port is an opening, and is, generally, larger in size, in terms of overall area, than the size of the air inlet.

Referring now to FIG. 1, the air inlet 14 is positioned at one end or terminus of casing 10, whereas the powder delivery port 54 is at the opposite end or terminus of casing 10.

The casings of this invention may be prepared by any means and may include, for example, designs which include two halves of the casing, which may be hermetically and permanently sealed, or in some embodiments, the casing may be of a single piece, for example, as prepared by molding or other conventional means.

In some embodiments, the inhaler devices of this invention are suitable for inhalation delivery by mouth, or nasal delivery. According to one aspect, and in one embodiment, the powder delivery port 54 is partially enclosed by or attached to a mouthpiece 12 (see, e.g., FIGS. 1, 2, 5 and 9), or in some embodiments, the delivery port 54 is partially enclosed by or attached to a nosepiece, which enables inhalation delivery via the mouth or nose.

In some embodiments, such choice between nasal or mouth delivery will reflect a consideration of the target area for delivery in the nasopharynx and other regions of the respiratory tree, or the particle size for delivery, or the age of the subject to which the inhaled powder is being administered, or a combination thereof.

In some embodiments, the air inlet 14 is positioned to be off center relative to a horizontal (i.e., longitudinal) axis, a vertical axis or a combination thereof of a side of the casing 10 containing the air inlet 14. For example, referring to FIGS. 4*a*-*d*, it is noted that the air inlet 14 is located in a lower half of side 56 relative to the longitudinal axis. Similarly, the air inlet 14 is located off-center relative to a vertical midline axis.

Figure 2:
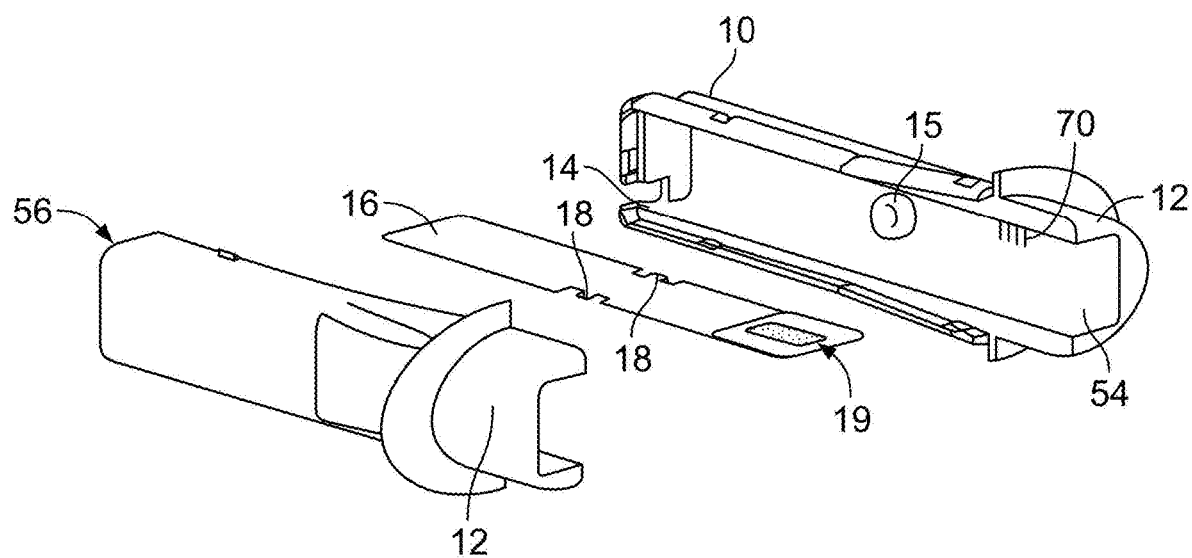
FIG. 2 shows an exploded perspective view of an embodied inhalation device wherein the dry-powder compartment and needle-like structure are illustrated.

Referring to FIG. 2, the casing 10 of the dry-powder inhaler devices of the present invention further include an elongated support panel 16 located within an interior cavity of the casing 10. The elongated support panel 16 resembles an elongated plate, and includes a first terminus and a second terminus opposite the first terminus. In some embodiments, the first terminus is located proximally to the air inlet 14, and the second terminus is located proximally to the powder delivery port 54. In certain embodiments, the elongated support panel 16 is fitted, or arranged, within the casing 10 such that the elongated support panel 16 partially rotates, angles or pivots, within the casing 10 about a single axis, shown as pivot axis 18.

In some embodiments, the casing 10, the support panel 16, or a combination thereof is substantially rectangular. In some embodiments, the casing 10, the support panel 16, or a combination thereof is substantially cuboidal, or in some embodiments, the casing 10, the support panel 16, or a combination thereof is substantially columnar, or in some embodiments, the casing 10, the support panel 16, or a combination thereof is substantially oval, in shape.

Figure 3A:
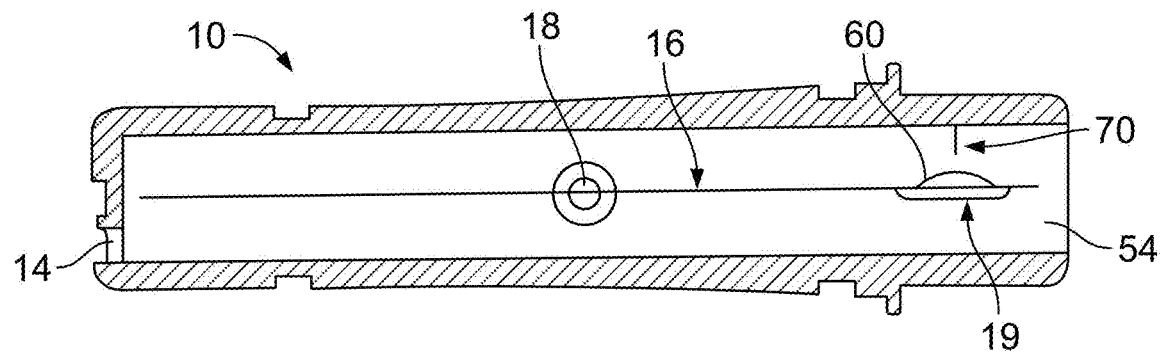
FIG. 3a shows a cross-sectional view of an embodied inhalation device wherein the dry-powder compartment and needle-like structure are illustrated.
Figure 3B:
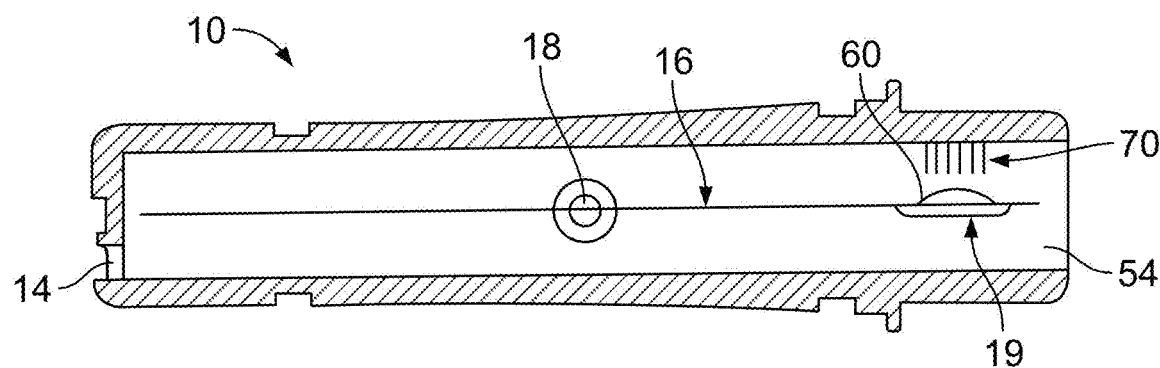
FIG. 3b shows a cross-sectional view of an alternate embodied inhalation device of FIG. 3a wherein the dry-powder compartment and a plurality of needle-like structures are illustrated.

Referring to FIGS. 3*a* and 3*b*, the longitudinal axis of the support panel 16 is preferably oriented in parallel to the longitudinal axis of the casing 10.

In some embodiments, a typical size range for the casing 10 of the present invention is between 5 cm and 15 cm in length, and with height and width dimensions in the 0.5 cm-2 cm range. The length and width of support panel 16 are set to closer fit the inner dimensions of this casing 10. It should be noted that the size of the casing 10 is not a limitation on the device.

Referring now to FIGS. 2, 3*a* and 3*b*, in some embodiments of the invention, the elongated support panel 16 comprises at least one compartment 19, located proximally to the second terminus of the support panel 16, near the powder delivery port 54 when positioned within the casing 10 as herein described. In alternative embodiments, the compartment 19 is located proximally to the first terminus of the support panel 16, near the air inlet 14. In some embodiments, support panel 16 will comprise the same material as that of the compartment 19, which may be formed of aluminum or some other suitable material, or in some embodiments, support panel 16 will comprise a different material than that of the compartment 19. In some embodiments, the compartment 19 is contiguous in structure with that of support panel 16, for example it has an indent for containing the medicament. In some embodiments, the compartment 19 is bonded, welded or otherwise attached to support panel 16.

In some embodiments, the at least one compartment 19 is a cavity that is filled with dry-powder medicament in an appropriate atmosphere and then sealed, e.g., by any suitable means as known in the art, such as is known in the field of packaging. In some embodiments, the dry-powder compartment 19 is covered and sealed by covering 60, such as aluminum, cellophane or other known blister-pack type coverings, and sealed as known in the art. Cover 60 of compartment 19 keeps the powdered medicament dry and uncontaminated. In certain embodiments, cover 60 is strong and durable enough to protect the medicament within compartment 19 from light, moisture and air, yet is capable of being punctured or ruptured by sharp device or object, to thereby allow the dry-powder 52 contained within compartment 19 to be released therefrom.

In certain embodiments, the casing 10 includes at least one sharp or pointed device 70 located on an internal surface thereof, proximal to the second terminus of the casing and near the powder delivery port 54, or proximal to the first terminus of the casing near the air inlet 14. In preferred embodiments, as shown in FIGS. 2, 3*a* and 3*b*, the at least one sharp or pointed device 70 is a region of needle- or pin-like structures 70 that may include one or more fins, pins, needles, edges, or other type of sharp or pointed needle- or pin-like structures that extend from the casing 10 in a direction transverse (i.e., perpendicular) to a longitudinal axis of the casing 10. In preferred embodiments, the region of needle- or pin-like structures 70 is suitable for puncturing or rupturing the blister sealed compartment 19.

In some embodiments of the present invention, as shown in FIG. 3*a*, there is only one needle-like structure 70. In other embodiments, as shown in FIG. 3*b*, there are two or more (i.e., a plurality) of needle-like structures 70. In other embodiments of the present invention, a region, such as protruding surface, of casing 10 includes a series, comb or bristle of needle-like structures 70 (see, for example, FIG. 3*b*). In this embodiment, the shape of the comb of needle-like structures 70 may substantially replicate or mimic the shape of the cover 60 over compartment 19 such that, as the support panel 16 rotates and the cover 60 strikes the structures 70, the series of needle-like structures 70 may produce a series of puncture holes, or pores, over substantially the entire surface area of the cover 60.

In preferred embodiments, the cover 60 may be fabricated from any suitable material as known in the art, such as, from an aluminum material, for example, aluminum or aluminum foil, aluminized foil, although the cover 60 may be fabricated from any suitable material that seals compartment 19 and is easily punctured or ruptured by the needle- or pin-like structures 70.

The support panel 16 located within the casing 10 is elongated and has a length sufficient that each terminus can abut or strike an interior surface of the casing 10 when rotated, angled or pivoted. Indeed, the support panel 16 is positioned within the casing 10 such that a first terminus of the support panel 16 is located proximally to the air inlet 14 while a second terminus of said support panel 16 is located proximally to said powder delivery port 54, such that a long axis of the support panel 16 is oriented in parallel to a longitudinal axis of the casing 10. In preferred embodiments, airflow through the device (i.e., air flowing from air inlets 14 towards powder delivery port 54 upon user inspiration) causes said elongated support panel 16 to partially rotate or pivot within said casing 10 about pivot axis 18 such that the second and/or first terminus of said support panel 16 will strike the interior surface of the casing 10, on the upper and lower internal surfaces thereof.

Figure 4A:
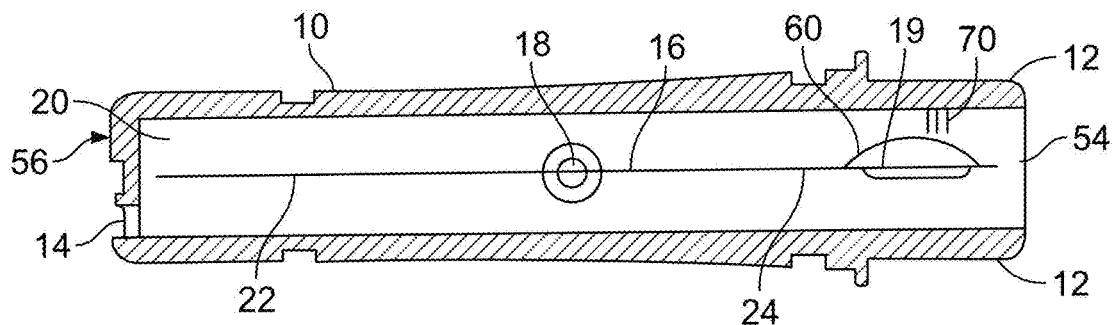
FIG. 4a shows a cross-sectional view of an embodied inhalation device, wherein the support panel is not blocking the airflow through said device.
Figure 4B:
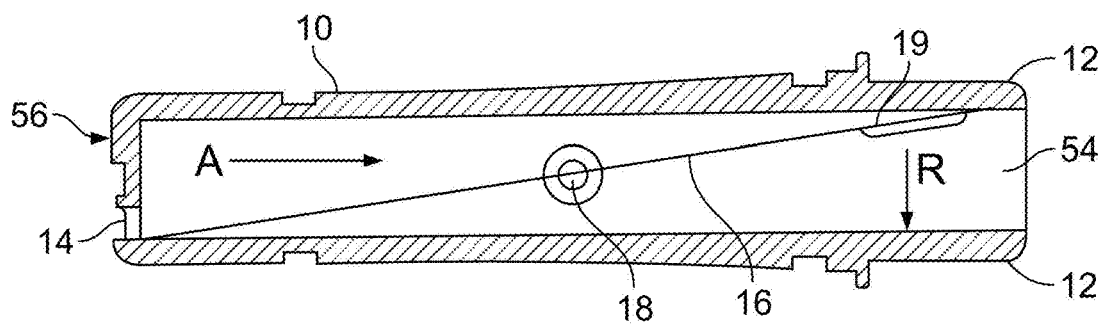
FIGS. 4b and 4c show cross-sectional views of an embodied inhalation device wherein the ends of the support panel proximal and distal to the inlet, respectively, may block the airflow through the device.
Figure 4C:
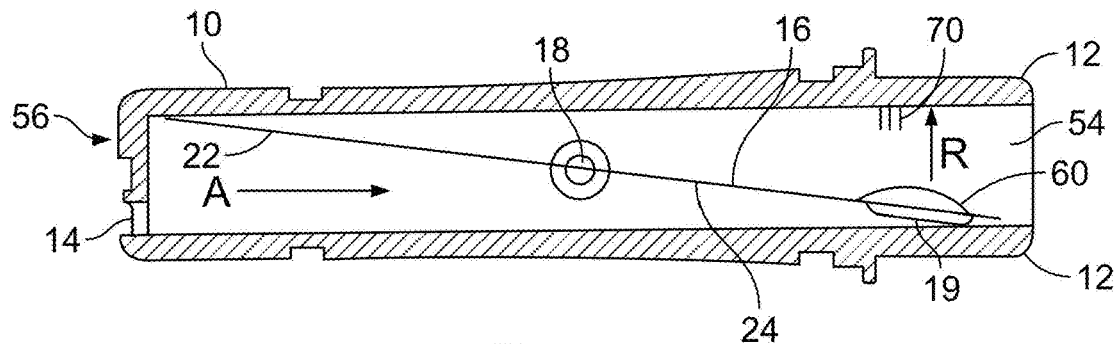

The principle of operation of an embodied device of the present invention is depicted in FIGS. 4*a*-*d*. A number of different possible states of the support panel 16 within the casing 10 are shown, as the support panel 16 partially rotates back and forth about pivot axis 18 due to an inhalation action, at the powder delivery port 54, which may be facilitated by the incorporation of a mouthpiece at its end. FIG. 4*a* shows a state in which the support panel is not blocking the airflow through the casing 10. Without being bound by theory, it is shown that the off-center positioning of the air inlet 14 creates turbulence in the area 20 between the inlet 14 and the portion 22 of the support panel 16 proximal to the air inlet 14. According to this aspect, the support panel 16 is tipped by the turbulence into one of the states shown in FIGS. 4b and 4c. Referring now to FIG. 4b, the support panel end 22 proximal to the air inlet 14 lowers, raising the support panel end 24 distal to the air inlet 14, resulting in some blocking of the airflow through the device. In one mechanism, the airflow (shown as "A"; FIGS. 4b and 2c) causes the support panel 16 to partially rotate, angle, pivot or rock in the direction shown by the arrow marked "R" (FIGS. 4b and 4c), which, in turn, causes the support panel 16 to partially rotate in an opposing direction, or flip to the configuration shown in FIG. 4c. Such partial rotation or flipping, may cycle (i.e., repeat), i.e. the airflow ("A") may cause the support panel 16 to flip back to its former state.

In some embodiments, such partial rotation, rocking or flipping of the support panel 16 within the casing 10 is accomplished due to a unique fitting of a lateral extension of the support panel 16, for example pivot axis 18 in FIG. 2, which is pivotally mounted within an appropriate housing, for example, 15 in FIG. 1b. In some embodiments, such casing 10 may also comprise a slit or rounded hole through a side wall thereof, into which such lateral extension may insert. Any other modification of the support panel 16 to allow for positioning of the support panel within the casing 10 and facilitating partial rotation of the support panel 16 may be considered as operable within this invention.

For example, in some embodiments of the present invention, the lateral extension of pivot axis 18 may be located at a mid-point (e.g., center) of support panel 16 such that, for example, there is equal distance between pivot axis 18 and the first and second termini of support panel 16 (e.g., the length of support panel 16 between pivot axis 18 and the first terminus is approximately equal to the length of support panel 16 between pivot axis 18 and the second terminus). In other embodiments of the present invention, the lateral extension of pivot axis 18 may not be at a center of support panel 16 (see, e.g., FIGS. 7c-d and 8c-d). In some embodiments, as depicted in FIGS. 7c-d and 8c-d, pivot axis 18 may be located proximal to the second terminus of support panel 16 such that the length of support panel 16 between pivot axis 18 and the first terminus is greater than the length of support panel 16 between pivot axis 18 and the second terminus. In other embodiments the opposite is true, and pivot axis 18 is located proximal to the first terminus of support panel 16.

Figure 4D:
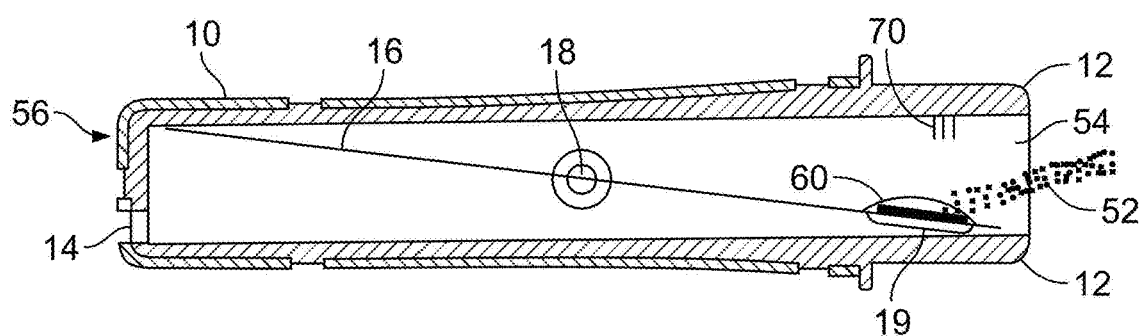
FIG. 4d shows a further cross-sectional view of an embodied inhalation device, showing some of the powder emerging from the punctured dry-powder compartment of the device after the cover of the dry-powder compartment has been punctured by the needle-like structures.
Figure 5:
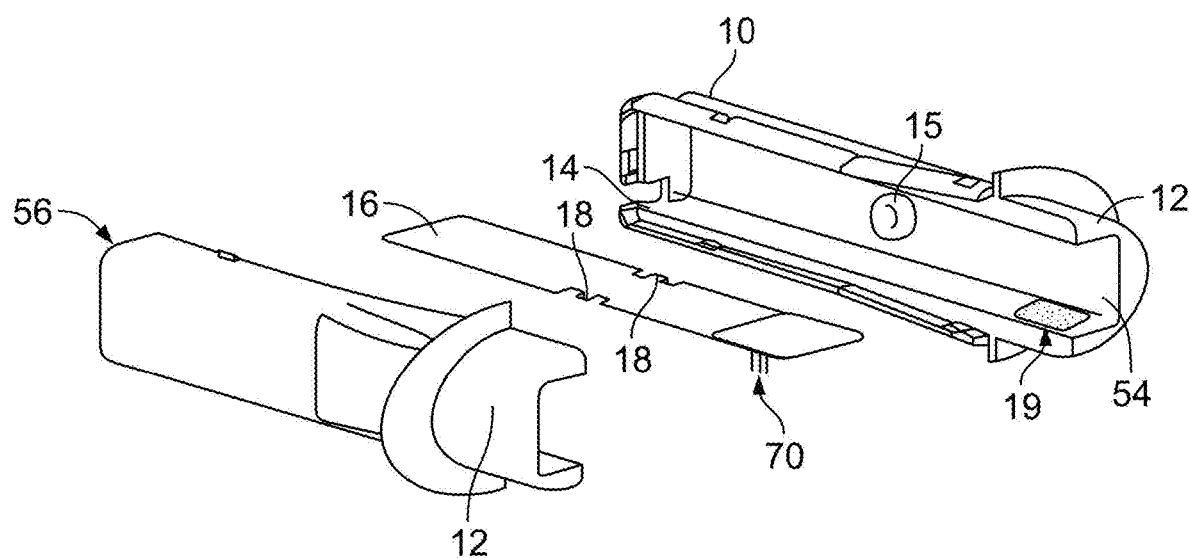
FIG. 5 shows an exploded perspective view of an alternate embodied inhalation device wherein the dry-powder compartment and needle-like structure are illustrated.

In preferred embodiments, a user's breathing action typically causes airflow through the device (i.e., air flowing from air inlets 14 towards powder delivery port 54 upon user inspiration), which causes said elongated support panel 16 to partially rotate or pivot within casing 10 about pivot axis 18 several times per second, in an up-and-down motion, thereby beating compartment 19 against casing 10. In preferred embodiments, due to the alignment of compartment 19 and the region of pin-like structures 70, the beating action of support panel 16 during inspiration causes the cover 60 covering compartment 19 to repeatedly strike the region of pin-like structures 70 provided on an internal surface of the casing 10, whereupon the needle-like structures 70 puncture or rupture the cover 60. As depicted in FIG. 4d, this repeated beating of compartment 19 against structures 70 causes the rupturing of cover 60, which allows the dry-powder drug or medicament within compartment 19 to be released therefrom and into the air flow space, from where it is inhaled into the user's throat and lung space.

Following repeat partial rotations, resulting in beating of the dry-powder containing compartment 19 distal to the air inlet 14 against one or more pin-like structures 70 provided on an internal surface of the casing 10, the powder contained within the compartment 19 emerges as free powder 52 into the airflow, which is drawn towards the powder delivery port 54 with mouthpiece 12. Without being bound by theory, as this free powder 52 emerges, it is disaggregated as a result of the sieving action of the holes or pores created in the cover 60 of compartment 19 by the action of the needle-like structures 70. In one embodiment, such hole-size for disaggregation to achieve dry-powder particles in the 1-5 micron diameter range is in the 10 micron to 70 micron range.

In certain embodiments, the pins, fins, edges, or needles 70 of the region puncture the cover 60, thereby or making holes therein or rendering the cover 60 porous.

In certain embodiments, the needles-like structures 70 are sized such as to create pores in the cover 60 of a size sufficiently large to enable the exit of the particles of dry-powder. In some embodiments, the pores have a pore size ranging from about 20 to 50 microns, which in some embodiments, is ideally sized for the release of a dry-powder drug having a diameter of about 1-5 microns. For a 3 micron diameter particle, for example, the pore size may range from between about 6 microns and 150 microns, or in some embodiments, between about 10 microns and 80 microns or in some embodiments between about 20 microns and 60 microns.

In some embodiments, according to this aspect, dry-powder exit from the inhaler device of this invention is facilitated by the beating action, or abutment of the support panel against an interior surface of the casing 10, which results in powder egress from the holes or pores created in the cover 60 by the needle- or pin-like structures 70.

In other embodiments, the interior surface of the casing 10 may include two or more regions of needle-like structures 70. For example, casing 10 may include one region of needle-like structures 70 on a top interior surface thereof and one region of needle-like structures 70 on a bottom interior surface thereof. Additionally, in this embodiment, the inhaler may include two or more covered compartments 19. In this embodiment, one covered compartment 19 is located on an upper surface of support panel 16 and aligned with the region of needle-like structures 70 located on the upper interior surface of casing 10, and one covered compartment 19 is located on the bottom surface of support panel 16 and aligned with the region of needle-like structures 70 located on the bottom interior surface of casing 10.

In the embodiments described above, the one or more region of needle-like structure(s) 70 is located on an interior surface of the casing 10, and the one or more covered compartment(s) 19 is located on support panel 16.

In other embodiments, support panel 16 may include the needle-like structures 70, and the interior surface of the casing 10 may include the dry-powder compartment 19. For example, it is possible to have one or more regions of needle-like structures 70 located on support panel 16 and the dry-powder compartment 19 located on an interior surface of casing 10 and aligned with the region of needle-like structures 70. For example, in certain embodiments, such as illustrated in FIG. 4a, support panel 16 may include a region of needle-like structures 70 protruding vertically upwards from a top surface of support panel 16, and aligned with a covered compartment 19 extending vertically downwards from a top interior surface of casing 10.

Figure 6A:
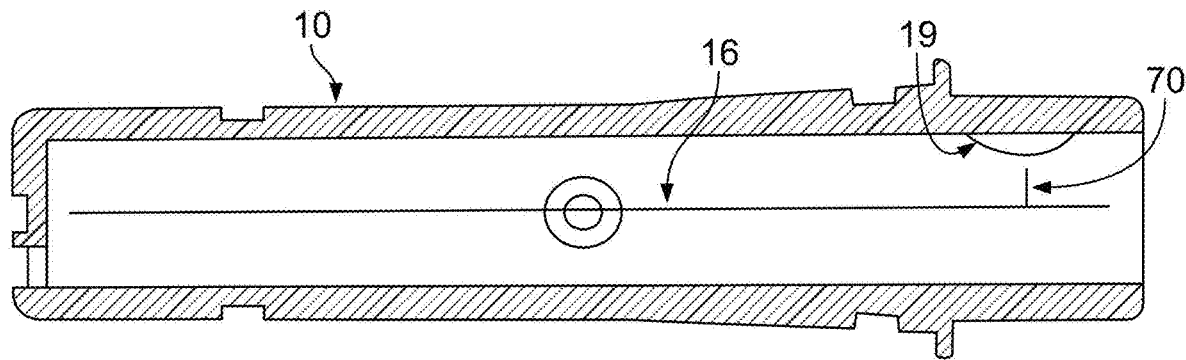
FIG. 6a shows a cross-sectional view of the alternate embodied inhalation device wherein the dry-powder compartment and needle-like structure are illustrated.
Figure 6B:
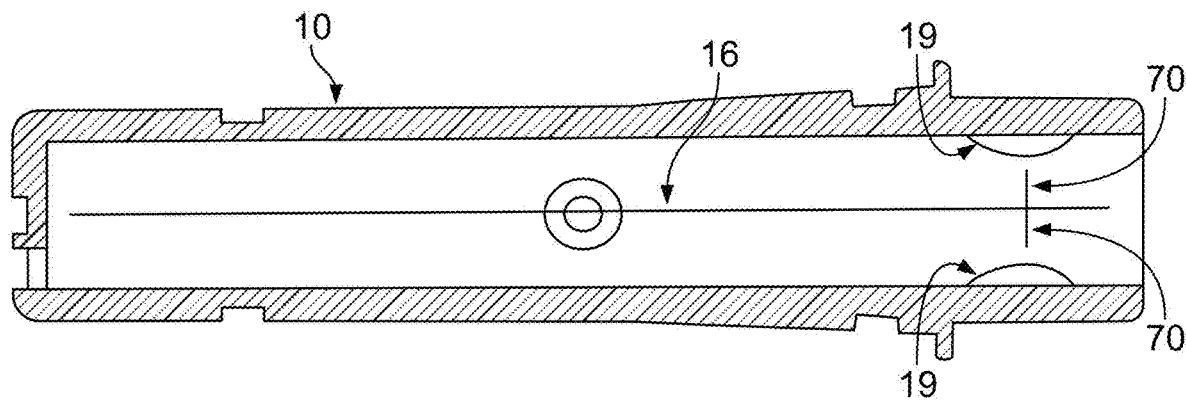
FIG. 6b shows a cross-sectional view of an alternate embodied inhalation device of FIG. 6a wherein two dry-powder compartments and two needle-like structures are illustrated.

However, in other embodiments, such as illustrated in FIG. 6b, support panel 16 may include one region of needle-like structures 70 on a top surface of support panel 16 and one region of needle-like structures 70 on a bottom surface of support panel 16. Additionally, in this embodiment, the inhaler may include two or more covered compartments 19. One covered compartment 19 located on a bottom interior surface of casing 10 and aligned with the region of needle-like structures 70 located on the bottom surface of support panel 16, and one covered compartment 19 located on the top interior surface of casing 10 and aligned with the region of needle-like structures 70 located on the top surface of support panel 16.

Figure 7A:
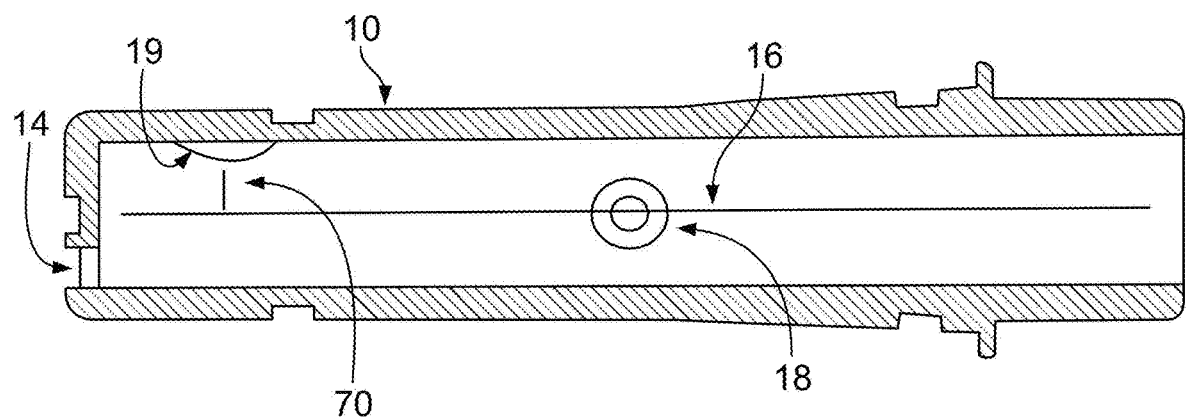
FIGS. 7a and 7b show cross-sectional views of an alternate embodied inhalation device wherein the dry-powder compartment and needle-like structure are illustrated.
Figure 7B:
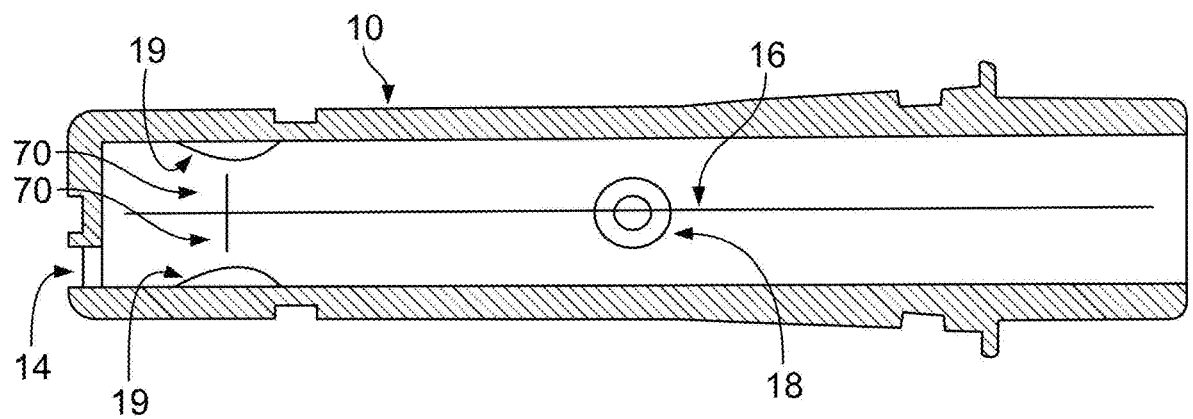

Referring now to FIGS. 7a to 7b, in certain embodiments of the present invention compartment 19 is located proximal to the first terminus near air inlet 14 on an interior surface of casing 10, and support panel 16 may include one or more regions of needle-like structures 70 on a top surface of support panel 16. In certain embodiments, as illustrated in FIG. 7a, the inhaler may include one covered compartment 19 on a top, interior surface of casing 10 extending vertically downwards toward support panel 16, and support panel 16 may include at least one needle-like structure 70 on a top surface of support panel 16 extending vertically upwards towards compartment 19 and cover 60. It is also contemplated, as illustrated in FIG. 7b, that compartment 19 may be located on a bottom interior surface of casing 10, and the at least one needle-like structure 70 may be located on a bottom surface of support panel 16.

Figure 7C:
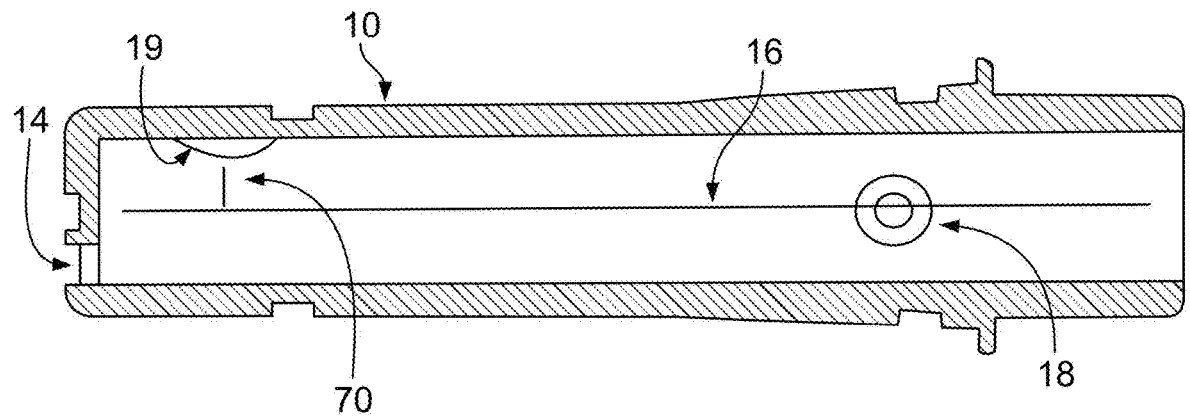
FIGS. 7c and 7d show cross-sectional views of an alternate embodied inhalation device wherein the dry-powder compartment and needle-like structure are illustrated.
Figure 7D:
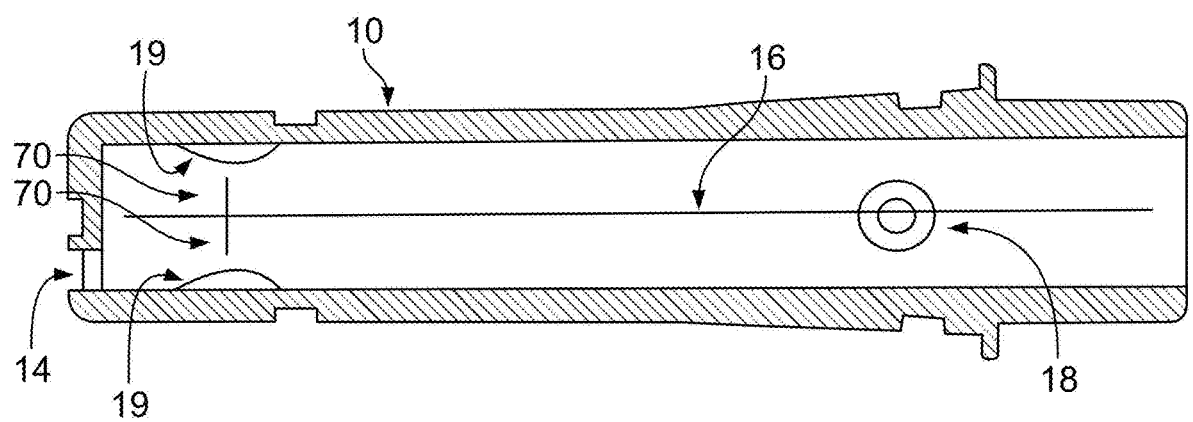

Referring now to FIGS. 7c and 7d, pivot axis 18 may also be located, rather than at a mid-point of support panel 16 (as shown in FIGS. 7a and 7b), proximal to the second terminus near drug delivery port 54. In this embodiment, the length of support panel 16 between pivot axis 18 and the first terminus is greater than the length of support panel 16 between pivot axis 18 and the second terminus. In this way, the length of support panel 16 is greater near air inlet 14, thereby allowing for more effective rotation of support panel 16 as air is inspired by a user.

Figure 8A:
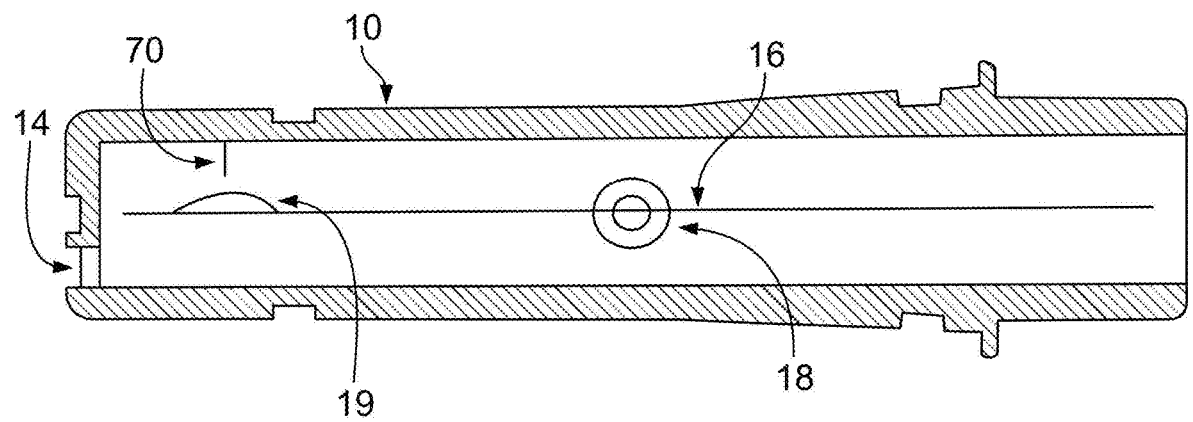
FIGS. 8a and 8b show cross-sectional views of an alternate embodied inhalation device wherein the dry-powder compartment and needle-like structure are illustrated.

Referring now to FIG. 8a, compartment 19 having cover 60 may be located on a top surface of support panel 16 proximal to the first terminus near air inlet 14, and at least one needle-like structure 70 is located on a top interior surface of casing 10 proximal to the first terminus near air inlet 14. In this embodiment, compartment 19 covered by cover 60 is provided on the top surface of support panel 16 and is aligned with the at least one needle-like structure 70, which extends vertically downward from the top interior surface of casing 10. As depicted in FIG. 8a, pivot axis 18 is located at a mid-point, or approximate center point, of support panel 16.

Figure 8B:
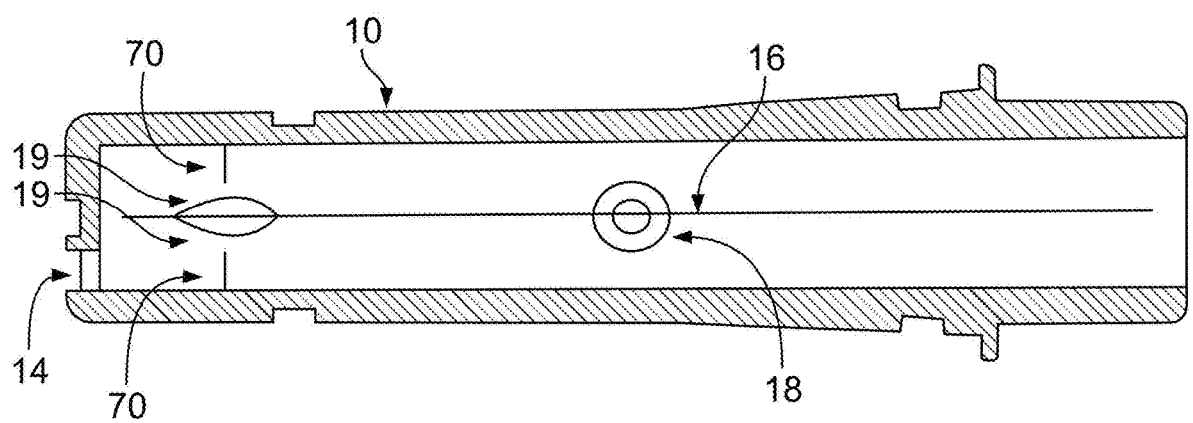

Referring now to FIG. 8b, compartment 19 covered by cover 60 may be located on each of the top and bottom surfaces of support panel 16 proximal to the first terminus near the air inlet 14. In this embodiment, at least one needle-like structure 70 is located on each of the top and bottom interior surfaces of casing 10, and each is aligned with the respective covered compartment 19 located on the top or bottom surface of support panel 16. As depicted in FIG. 8b, pivot axis 18 is located at a mid-point, or approximate center point, of support panel 16.

Figure 8C:
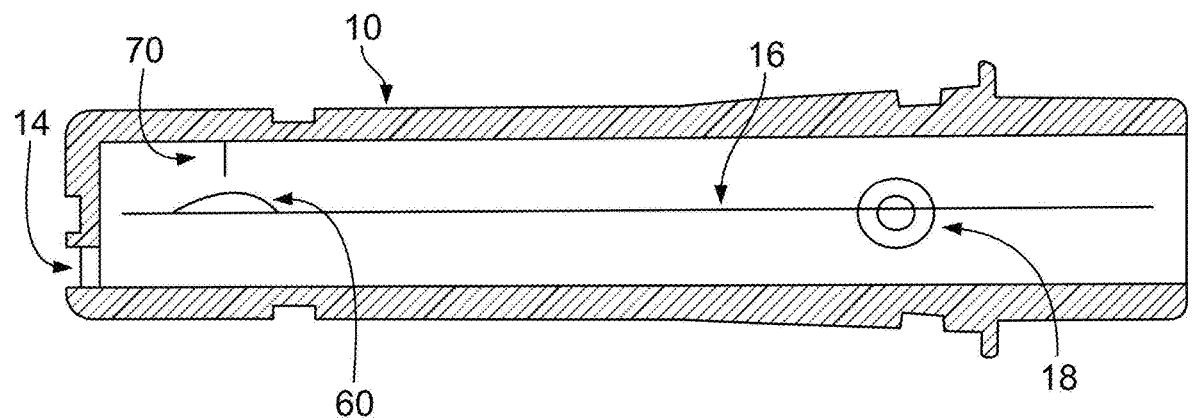
FIGS. 8c and 8d show cross-sectional views of an alternate embodied inhalation device wherein the dry-powder compartment and needle-like structure are illustrated.

Referring now to FIG. 8c, compartment 19 having cover 60 may also be located on a top surface of support panel 16 proximal to the first terminus near air inlet 14, and at least one needle-like structure 70 may be located on a top interior surface of casing 10 proximal to the first terminus near air inlet 14. In this embodiment, compartment 19 covered by cover 60 is provided on the top surface of support panel 16 and is aligned with the at least one needle-like structure 70, which extends vertically downward from the top interior surface of casing 10. As depicted in FIG. 8c, pivot axis 18 may be located proximal to the second terminus of support panel 16, thereby creating a greater length of support panel 16 between pivot axis 18 and the first terminus, and a shorter length of support panel 16 between pivot axis 18 and the second terminus. The greater length of support panel 16 between pivot axis 18 and the first terminus allows for more effective rotation of support panel 16 as air is inspired by a user.

Figure 8D:
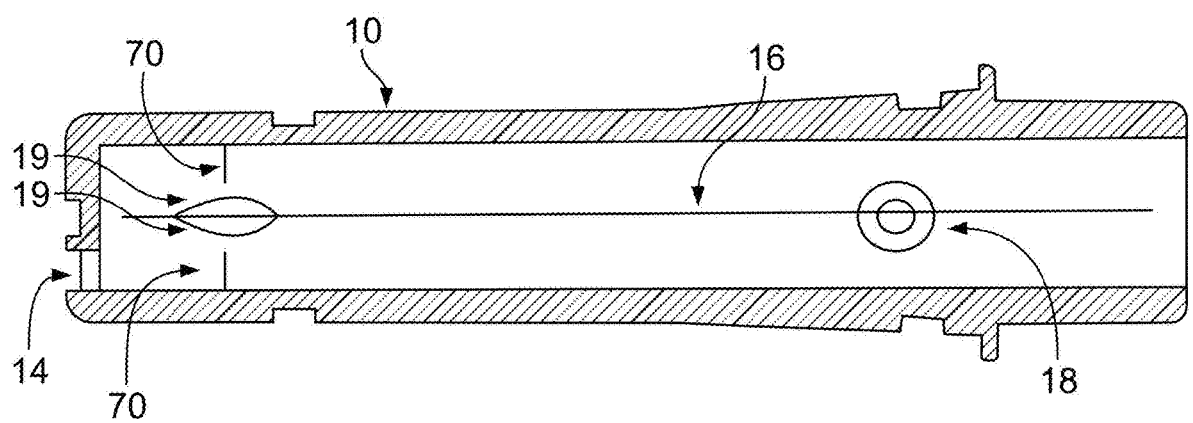

Referring now to FIG. 8d, compartment 19 covered by cover 60 may be located on each of the top and bottom surfaces of support panel 16 proximal to the first terminus near the air inlet 14. In this embodiment, at least one needle-like structure is located on each of the top and bottom interior surfaces of casing 10, and each is aligned with the respective compartment 19 located on the top and bottom surfaces of support panel 16. As depicted in FIG. 8d, pivot axis 18 is located proximal to the second terminus of support panel 16, thereby creating a greater length of support panel 16 between pivot axis 18 and the first terminus, and a shorter length of support panel 16 between pivot axis 18 and the second terminus. The greater length of support panel 16 between pivot axis 18 and the first terminus allows for more effective rotation of support panel 16 as air is inspired by a user.

Figure 9:
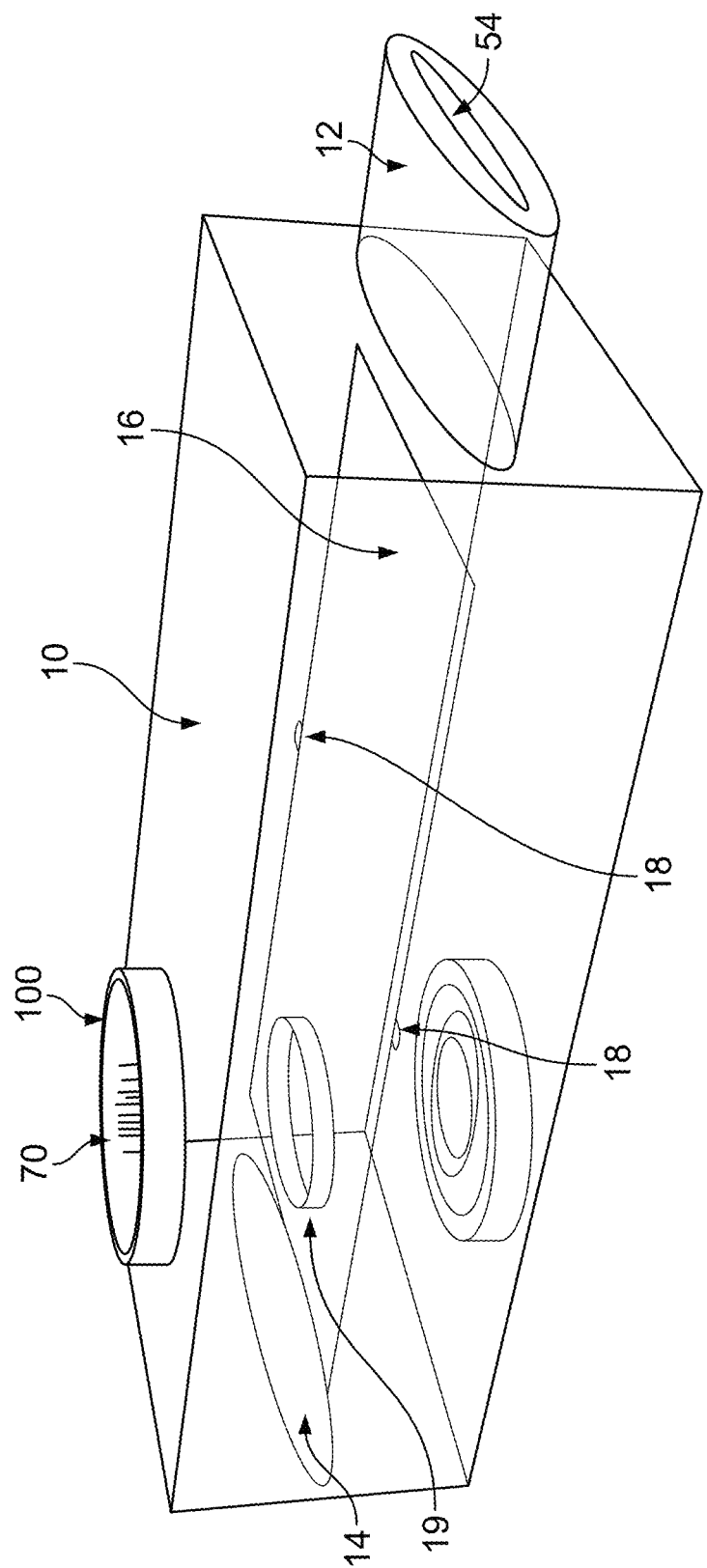
FIG. 9 shows a perspective view of an alternate embodied inhalation device wherein the dry-powder compartment, the needle-like structure(s), and the push button(s) are illustrated.

FIG. 9 depicts an alternate embodied inhalation device according to certain aspects of the present invention. The embodiment of the inhalation device illustrated in FIG. 9 is similar to the embodiments of the inhalation devices discussed above in that it includes, inter alia, a casing 10, an air inlet positioned at one terminus of casing 10, and a powder delivery port 54 partially enclosed by or attached to a mouth piece 12 positioned at another terminus of casing 10, an elongated support panel 16 having a pivot axis 18 and a dry-powder compartment 19, and at least one region of needle-like structure(s) 70.

While not specifically depicted in FIG. 9, air inlet 14 may be positioned off center relative to a horizontal (i.e., longitudinal) axis, a vertical axis or a combination thereof of a side of the casing 10 containing the air inlet 14 (see FIGS. 4a-d). Similarly, the air inlet 14 may be located off-center relative to a vertical midline axis.

Support panel 16 is located within an interior cavity of casing 10 and resembles an elongated plate, although other shapes are contemplated. Support panel 16 includes a first terminus and a second terminus opposite the first terminus. In some embodiments, the first terminus is located proximally to the air inlet 14, and the second terminus is located proximally to the powder delivery port 54. In certain embodiments, the elongated support panel 16 is fitted, or arranged, within casing 10 such that the elongated support panel 16 partially rotates, angles or pivots, within casing 10 about a single axis, shown as pivot axis 18.

In the embodiment depicted in FIG. 9, pivot axis 18 includes at least two lateral extensions and is located at a mid-point or approximate center of support panel 16. However, pivot axis 18 may be located at any point along a longitudinal axis of support panel 16, such as discussed above with reference to, inter alia, FIGS. 7c-d and 8c-d. For example, in some embodiments, pivot axis 18 may be located proximal to the second terminus of support panel 16, thereby creating a greater length of support panel 16 between pivot axis 18 and the first terminus, and a shorter length of support panel 16 between pivot axis 18 and the second terminus. It is contemplated that pivot axis 18 may also be located proximal to the first terminus.

In the embodiment depicted in FIG. 9, elongated support panel 16 comprises at least one compartment 19 located proximally to the first terminus of the support panel 16, near air inlet 14 when positioned within the casing 10 as herein described. Positioning the dry-powder compartment 19 near air inlet 14 (e.g., away from drug delivery port 54 and mouthpiece 12) increases the distance that the dry-powder therapeutic must travel, thereby allowing the dry-powder to accelerate as it traverses the interior cavity of the inhaler and enters the mouth and lungs. In alternative embodiments, the compartment 19 may be located proximally to the second terminus of the support panel 16, near the drug delivery port 54.

In some embodiments, compartment 19 is contiguous in structure with that of support panel 16, for example support panel 16 has an indent, forming compartment 19 for containing the medicament. In some embodiments, compartment 19 is bonded, welded or otherwise attached to support panel 16. In preferred embodiments, compartment 19 is covered and sealed by covering 60, such as aluminum, cellophane or other known blister-pack type coverings, and sealed as known in the art and as discussed above. In certain embodiments, cover 60 is capable of being punctured or ruptured by a sharp device or object (e.g., needle-like structure(s) 70), to thereby allow the dry-powder drug or medicament contained within compartment 19 to be released therefrom.

In certain embodiments, casing 10 includes at least one sharp or pointed device 70 located on an internal surface thereof, proximal to the first terminus of casing 10 near air inlet 14, or proximal to the second terminus of casing 10 near drug delivery port 54. In preferred embodiments, as shown in FIG. 9 and discussed above, the at least one sharp or pointed device 70 is a region of needle- or pin-like structures 70 that may include one or more fins, needles, edges, or other type of sharp or pointed needle- or pin-like structures extending in a direction transverse (e.g., perpendicular) to a longitudinal axis of casing 10. In preferred embodiments, the region of needle- or pin-like structures 70 is suitable for puncturing or rupturing the cover 60 that seals compartment 19.

It is contemplated, however, that having the needle- or pin-like structures 70 constantly exposed within the interior cavity of the casing may hinder the operation of the inhalation device. For example, the needles may hinder the free rotation of the elongated support panel about its axis during inspiration. In another example, the needles may hinder the release of the dry-powder from the dry-powder compartment. Also, there may be vibration interference in the release of the drug or medicament from the covered compartment 19 because the needles stay at the same extended position and continue to touch the drug compartment cover 60 with each vibration of the elongated support panel 16. Accordingly, in certain embodiments of the present invention it is desirable that the needles be configured to extend into and retract from the interior cavity of the casing, such that the user extends the needle- or pin-like structures 70 to puncture the cover 60 of the drug compartment 19, and then retracts them, just prior to inhalation. In this way, the needles may still operate to puncture the dry-powder compartment while avoiding the issues associated therewith.

In some embodiments, such as depicted in FIG. 9, casing 10 includes at least one push button 100 to actuate the needle- or pin-like structures 70, although it is contemplated that casing 10 may include two or more (e.g., a plurality) of push buttons 100. Push buttons 100 are discussed in more detail below with reference to FIGS. 10a-b.

In preferred embodiments, push button 100 is configured to communicate with the interior cavity of casing 10 in such a way that an object, specifically one or more needle- or pin-like structures 70, may pass unhindered from push button 100 into the interior cavity of casing 10, and vice versa. As discussed in more detail below, in some embodiments a region of needle-like structures 70 may pass unhindered from push button 100 into the interior cavity of casing 10. In certain embodiments, push button 100 may be constructed, as known in the art, such as by including a spring (e.g., coiled spring or leaf-spring), such that compressing push button 100 extends the region of needle-like structures into the interior cavity, and releasing the push button 100 retracts the region of needle-like structures from the interior cavity.

As shown in FIG. 9, certain embodiments of the present invention may include, without limitation, two push buttons 100. In these embodiments, casing 10 may include a first push button located on a first external surface thereof and a second push button located on a second external surface opposing the first external surface (as depicted in FIG. 9). In one embodiment, both the first push button 100, located, for example, on a top surface of casing 10, and the second push button 100, located, for example, on a bottom surface of casing 10, include the needle-like structures 70, and both push buttons 100 operate to puncture compartment 19.

In another embodiment, only the first push button 100, located, for example, on a top surface of casing 10, includes one or more needle- or pin-like structures 70, while the second push button 100, located, for example, on a bottom surface of casing 10, does not include the needle-like structures. Of course, the first push button 100 which includes one or more needle- or pin-like structures 70 may be located on a bottom surface of casing 10, while the second push button 100 which does not include the needle-like structures 70 may be located on a top surface of casing 10. (It should be understood, in these embodiments, that the location on casing 10 where push button 100 is situated should be opposite to where on the surface of the support panel 16 the compartment 19 containing the drug or medicament is situated.) In this embodiment, only the first push button 100 operates to puncture compartment 19, while the second push button 100 is configured as a support button.

In some embodiments push button(s) 100 may be contiguous in structure with that of casing 10. In other embodiments, push button(s) 100 may be embedded, bonded, welded or otherwise attached to an external surface of casing 10. Attachment points other than an external surface of casing 10 are contemplated. In preferred embodiments, push button 100 is aligned with compartment 19 on support panel 16 such that the beating action of support panel 16 during inspiration causes the cover 60 covering dry-powder compartment 19 to strike in the approximate area of push button 100.

Figure 10A:
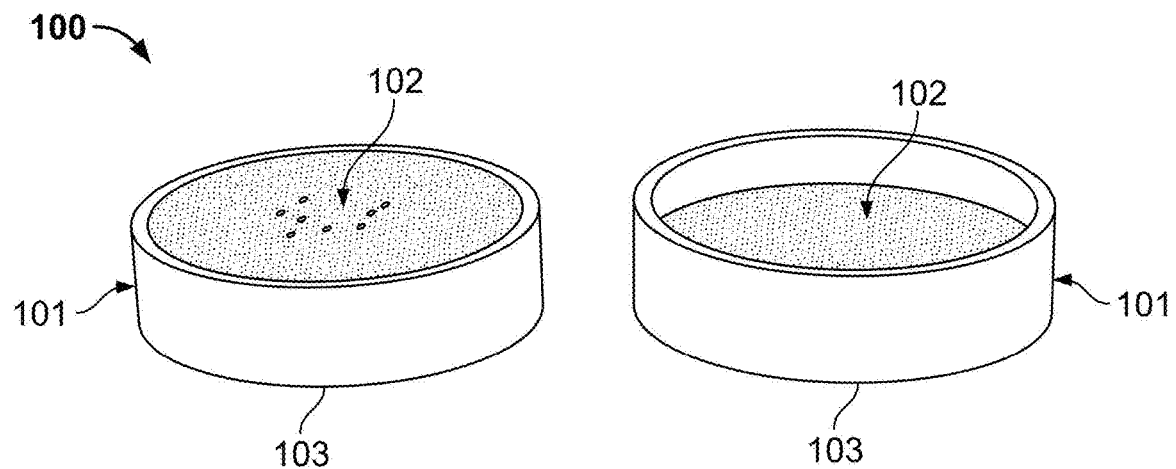
FIGS. 10a and 10b are illustrations of several views of a push button according to certain embodiments of the present invention.
Figure 10B:
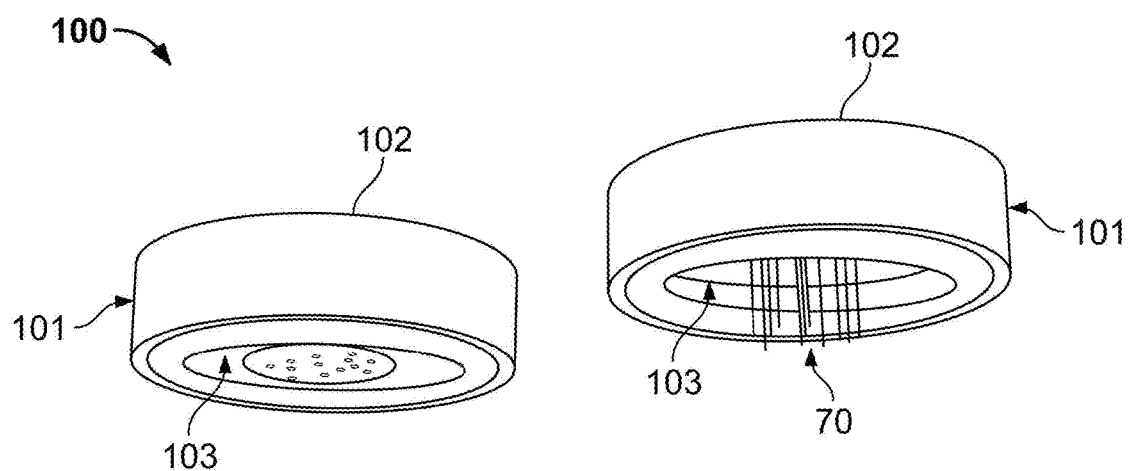

Reference is now made to FIGS. 10a and 10b, which are illustrations of several views of a push button 100 according to aspects of certain embodiments of the present invention. FIG. 10a is a top view of push button 100 in an undepressed (left) and depressed (right) configuration. FIG. 10b is a bottom view of push button 100 in an undepressed (left) and depressed (right) configuration. In certain embodiments, push button 100 may include a housing 101, a top panel 102, and a (e.g., internal) spring mechanism (not shown in FIG. 10a or 10b).

In preferred embodiments, bottom opening 103 of housing 101 is configured to communicate with the interior cavity of casing 10 in such a way that an object may pass unhindered from housing 101 through opening 103 into the interior cavity of casing 10, and vice versa. For example, a region of needle-like structures 70 may pass unhindered from push button 100 into the interior cavity of casing 10. In certain embodiments, opening 103 may be an opening in casing 10, and push button 100 (or, in other embodiments, a puncture mechanism 200) may be located above/on top of or below/under (e.g., vertically aligned with) the casing's opening 103, such that a region of needle-like structures 70 of push button 100 may pass unhindered from push button 100 into the interior cavity of casing 10.

In some embodiments, housing 101 of push button 100 may be any desired shape (e.g., cylindrical) and may include an outer periphery, an inner periphery, a top opening, a bottom opening, as well as having a height and a width, thereby enclosing a volume. In other embodiments, where needle-like structures 70 are not used, no housing 101 for push button 100 is required, as push button 100 could be in the form of a leaf or hinge, as described hereinbelow, which could be in the form of a one-unit mold, made, e.g., from plastic.

In preferred embodiments, the volume of housing 101 of push button 100 is sufficient to encompass or enclose (either partially or completely) at least one region of needle-like structures 70 when push button 100 is in an undepressed state (see left side of FIGS. 10a and 10b). In some embodiments, the needle-like structures 70 are entirely enclosed within housing 101, and no portion of the needle-like structures 70 extends into the interior cavity of casing 10 when push button 100 is in an undepressed state. In other embodiments, at least a portion of the needle-like structures 70 extends out of housing 101 into the interior cavity of casing 10 when push button 100 is in an undepressed state. In preferred embodiments, housing 101, including at least one region of needle-like structures 70 contained therein, is aligned with dry-powder compartment 19 on support panel 16 such that the beating action of support panel 16 during inspiration causes dry-powder compartment 19 to strike the region of needle-like structures 70, whereupon the needle-like structures 70 puncture or rupture cover 60 covering dry-powder compartment 19.

In certain embodiments, top panel 102 of push button 100 includes a top surface and a bottom surface and is sufficiently sized to fit within the inner periphery of housing 101. In preferred embodiments, top panel 102 may be substantially flat, although alternative embodiments wherein top panel 102 is not substantially flat are contemplated. Top panel 102 may be configured as a depressible button, such that a user may press on a top surface of top panel 102 and depress top panel 102 into housing 101. The user may then release top panel 102 to allow top panel 102 to return to an undepressed position.

In preferred embodiments, push button 100 includes a (e.g., internal) spring mechanism (e.g., a coiled spring or a leaf-spring) configured to extend at least one region of needle-like structures 70 therefrom when depressed and to retract the at least one region of needle-like structures 70 therein when released. The spring mechanism may be attached to a bottom surface of top panel 102 inside housing 101 to facilitate or assist the depress-ability of top panel 102. For example, in certain embodiments the spring mechanism may be attached to an outer peripheral area, and a region of needle-like structures 70 may be attached at a central area, on the bottom surface of top panel 102.

In this way, a user may depress push button 100 by applying a downward force on the top surface of top panel 102, causing the spring mechanism to compress and moving the region of needle-like structures 70 in a downwards motion. The downwards motion of the region of needle-like structures 70 may expose the region of needle-like structures 70 to the interior cavity of casing 10 (see the right sides of FIGS. 10a and 10b). The user may release the downward force on the top surface of top panel 102 of push button 100, causing the spring mechanism (e.g., a coiled spring or a leaf-spring) to expand and retract the region of needle-like structures 70 back into push button 100 in an upwards motion. The upwards motion of the region of needle-like structures 70 may retract the region of needle-like structures 70 from the interior cavity of casing 10 (see left sides of FIGS. 10a and 10b). Similar methods of use may be applied to an inhaler device having a puncture mechanism 200 as discussed elsewhere herein.

For example, in certain embodiments, and without limitation, casing 10 of the inhalation device of the present invention may have a width perpendicular to the longitudinal axis of approximately 0.6-0.8 cm. Housing 101 of push button 100 may have a height of approximately 0.5 cm, and the spring mechanism may be housed within the volume of housing 101 and also have a height of approximately 0.5 cm. Additionally, each needle (e.g., pin, nail, etc.) of the region of needle-like structures 70 may have a height of approximately 0.5 cm. In operation, a user may compress the spring mechanism from approximately 0.5 cm to approximately 0.2 cm thereby exposing approximately 0.3 cm of each needle to the interior cavity of casing 10.

As discussed, push button 100, which may be more broadly defined as a puncture mechanism 200, includes a spring mechanism or living hinge configured to extend at least one region of needle-like structures 70 therefrom when depressed and to retract the at least one region of needle-like structures 70 therein when released.

Figure 11A:
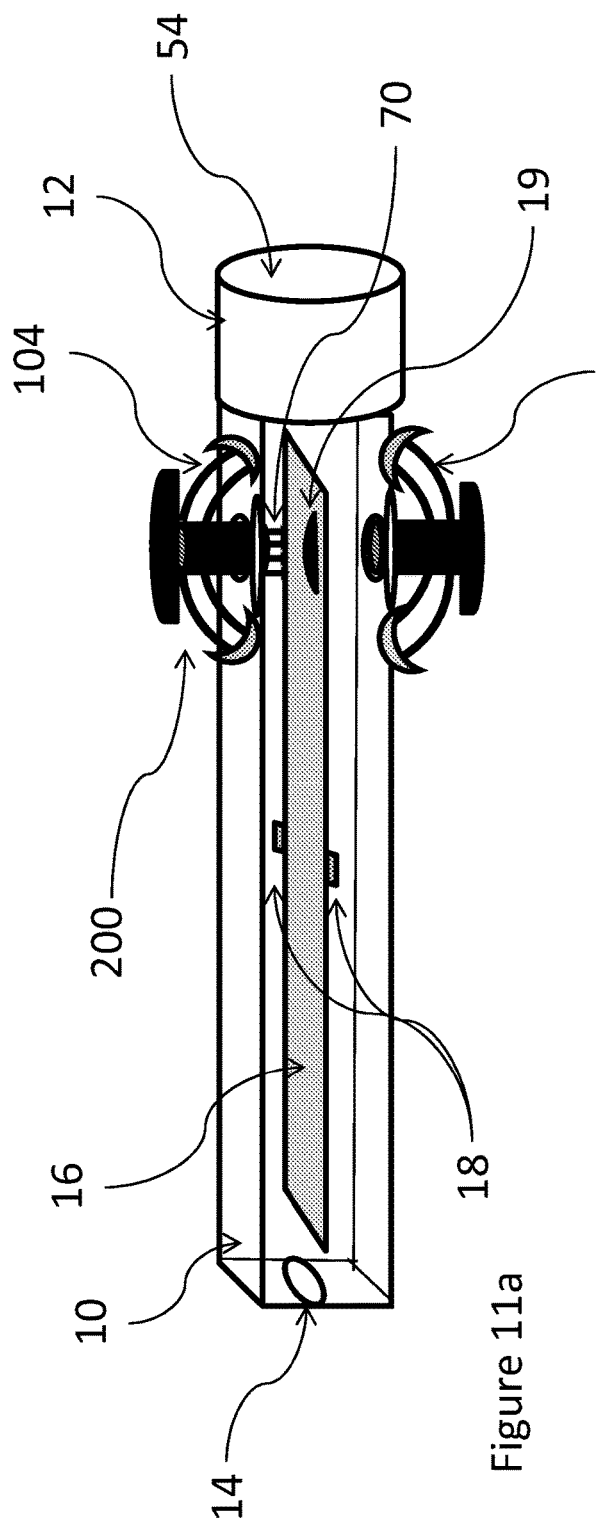
FIGS. 11a and 11b show perspective views of a push button having a leaf-spring mechanism according to certain embodiments of the present invention.
Figure 11B:
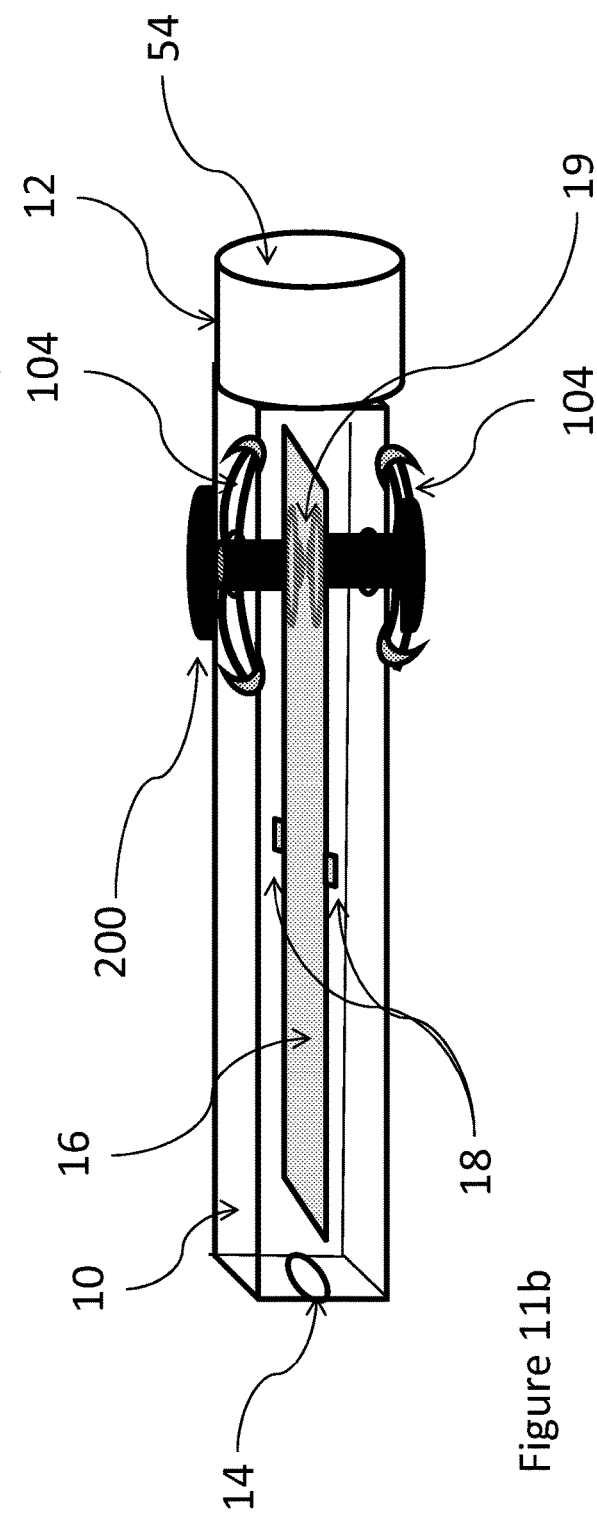

Reference is now made to FIGS. 11-12, which illustrate perspective views of puncture mechanism 200 (e.g., a spring-loaded puncture mechanism) having different types of spring mechanisms according to certain aspects of the present invention. FIG. 11a is a perspective view illustrating top and bottom puncture mechanisms 200 with a leaf-spring assembly 104 in an undepressed, i.e., released, state, while FIG. 11b is a perspective view illustrating top and bottom puncture mechanisms 200 with the leaf-spring assembly 104 in a depressed state. FIG. 12a is a perspective view illustrating top and bottom puncture mechanisms 200 with a coiled spring 105 in an undepressed, i.e., released, state, while FIG. 12b is a perspective view illustrating top and bottom puncture mechanisms 200 with the coiled spring 105 in a depressed, i.e., activated, state.

Figure 13A:
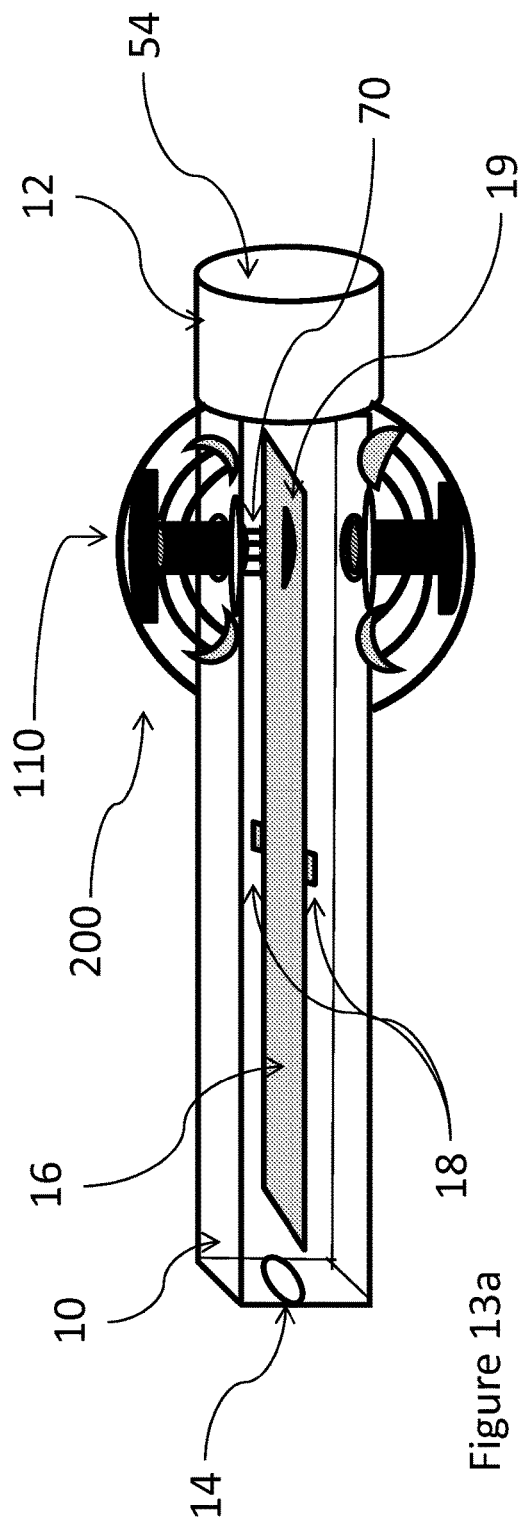
FIGS. 13a and 13b show perspective views of a dry-powder inhaler having a cover over the push buttons according to certain aspects of the present invention.
Figure 13B:
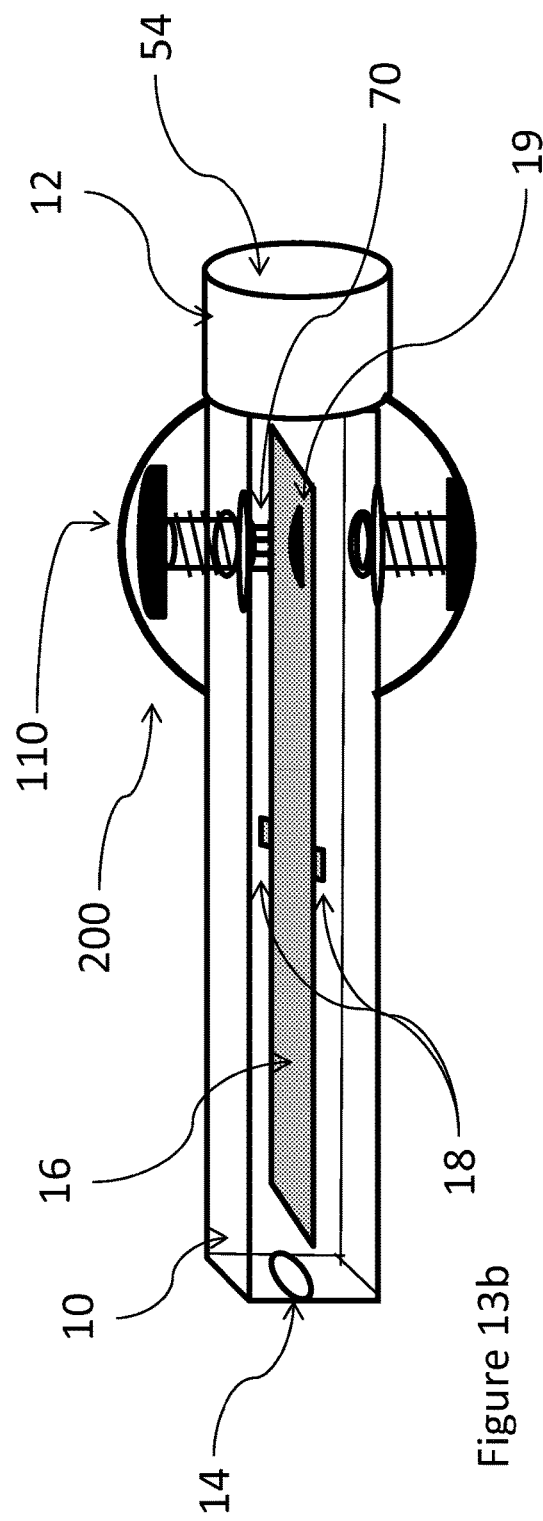

As discussed, housing 101 of push button 100 may have any desired shape, not just cylindrical as shown in FIGS. 9, 10a and 10b. Reference is now made to FIGS. 13a and 13b, which are perspective views illustrating a dry-powder inhaler having a cover over push buttons 100 (or puncture mechanism 200) according to certain aspects of the present invention. FIG. 13a is a perspective view illustrating casing 10 of dry-powder inhaler having the leaf-spring assembly 104, such as illustrated in FIGS. 11a and 11b, and having cover 110 covering puncture mechanism 200. FIG. 13b is a perspective view illustrating casing 10 of dry-powder inhaler having the coiled spring 105, such as illustrated in FIGS. 12a and 12b, and having cover 110 covering puncture mechanism 200.

In certain embodiments, puncture mechanism cover 110 may have features similar to push button housing 101 such that cover 110 may include an outer periphery, an inner periphery, a bottom opening (e.g., bottom opening 103), as well as a height and a width, all as desired, thereby enclosing a volume. In an alternative embodiment, casing 10 includes both a housing 101 and a cover 110, wherein cover 110 covers at least a portion of housing 101.

In preferred embodiments, the volume of cover 110 is sufficient to encompass or enclose (either partially or completely) a puncture mechanism 200, including any needle- or pin-like structures 70 associated with puncture mechanism 200. Puncture mechanism cover 110 may also be large enough to accommodate a push button 100 housing 101 in certain embodiments.

Figure 14:
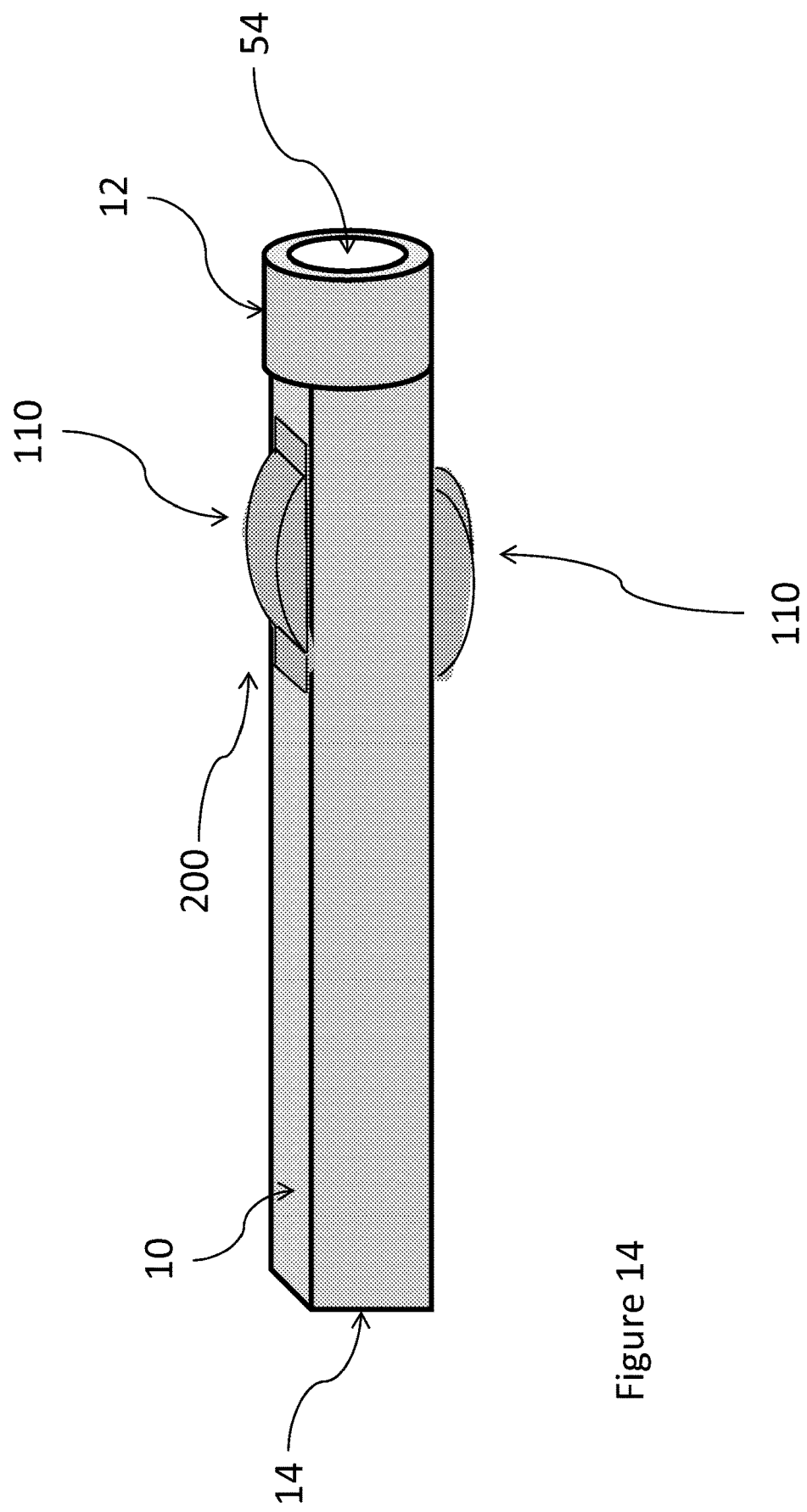
FIG. 14 shows an external view of a dry-powder inhalation device having a cover according to certain embodiments of the present invention.

In certain embodiments, cover 110 may be located on an external surface of casing 10. Cover 110 may be connected to, or otherwise associated with, the external surface of casing 10 at the edges of cover 110, and any number of connecting edges or portions is contemplated and is not limiting on the present invention. In certain embodiments, a first portion (e.g., a first edge) of cover 110 may connect to, or otherwise associate with, a surface of casing 10, extend over (e.g., cover) puncture mechanism 200, and connect again to the surface of casing 10 via a second portion (e.g., a second edge) of cover 110, as illustrated schematically in, for example, FIGS. 13a and 13b. Alternatively, according to certain embodiments of the present invention, FIG. 14 illustrates cover 110 as it might appear from an outside view on an external surface of casing 10.

In certain embodiments, cover 110 may have a domed shape such as, for example, the shape of cover 110 illustrated in FIGS. 13a and 13b. In other embodiments, cover 110 may have a slanted shape having an elongated slanted portion having a face facing in a direction towards mouthpiece 12. In yet other embodiments, such as illustrated in FIG. 14, cover 110 may have a curved shape having a curved or slanted face facing in a direction towards mouthpiece 12. Other shapes of push button cover 110 are contemplated. As discussed in more detail below, the shape and structure of cover 110 is not just for aesthetic purposes, but also includes a functional and ergonomic purpose.

Cover 110 may be made of a soft or semi-rigid material such as, for example, a soft or semi-rigid plastic or rubber material, so that cover 110 is sufficiently flexible and malleable in order to allow a user to press on cover 110, thereby depressing the puncture mechanism 200 located under the cover 110, and in turn thereby extending the at least one region of needle- or pin-like structures 70 into the interior cavity of casing 10. In preferred embodiments, the material of cover 110 is flexible or elastic enough to allow cover 110 to return or rebound to an undepressed, i.e., released, position, such that the puncture mechanism 200 is also allowed to return to an undepressed, i.e., released, position (e.g., via the internal coil spring or leaf-spring assembly), and in turn thereby retracting the at least one region of needle- or pin-like structures 70 from the interior cavity of casing 10.

In certain embodiments, it may not be necessary to have separate structures or parts that together comprise puncture mechanism 200, such as leaf-spring assembly 104, coiled spring 105, needle- or pin-like structures 70, and cover 110. Instead, it may be preferable to form puncture mechanism 200 such that it includes the hinges and leaf springs, as well as pin-like structures 70, integrated therein as part of its plastic mold. Alternatively, or in addition, it may be preferable to form casing 10 such that it includes puncture mechanism 200, including its the hinges and leaf springs, as well as pin-like structures 70, integrated therein as part of its plastic mold.

In certain embodiments, as discussed hereinbelow, puncture mechanism 200 may include a spring assembly or a living hinge assembly and may be actuated to extend the at least one region of needle- or pin-like structures 70 in the interior cavity of casing 10 after the puncture mechanism 200 is struck or pressed by an obstruction upon the inhaler device being pulled from a dispenser or from a compartment (e.g., a slot) of an inhaler kit.

Puncture mechanism 200 may have other configurations that are configured to extend at least one region of needle-like structures 70 therefrom when depressed and to retract the at least one region of needle-like structures 70 therein when released. Reference is now made to FIGS. 15a and 15b, which are perspective views of a puncture mechanism 200 having a living hinge assembly 106 according to certain aspects of the present invention. Living hinge assembly 106 may be formed directly from casing 10 as known in the art, or may be formed separate and distinct from the casing. Specifically, in one embodiment, living hinge assembly 106 typically includes a portion (e.g., a plate) 109 of casing 10 that is cut at three edges, leaving a fourth edge attached. The fourth edge of plate 109 may be thin relative to the thickness of casing 10, and may be scored, thus forming a living hinge and allowing the cut-out portion (e.g., the plate) to pivot about the living hinge, which is the connection point at the fourth (e.g., connected) edge.

In other embodiments, for example as shown in FIGS. 21a and 21b, plate 109 of living hinge assembly 106 may be a separate piece distinct from casing 10. In this embodiment, plate 109 may be attached to casing 10 via an attachment flange 89. Plate 109 may be connected to the attachment flange 89 via a curved, flexible portion 87, which operates as the living hinge.

In certain embodiments, the puncture mechanism 200 with the living hinge assembly 106 may include many of the same, or similar, features of the embodiments of puncture mechanism 200 or push button 100 discussed above such as, for example, the location relative to mouthpiece 12 and air inlet 14, the location relative to pivot axis 18, as well as the location relative to the location of dry-powder compartment 19 on support panel 16.

In certain embodiments, the length of the plate 109 of living hinge assembly 106 may be relatively short such that the plate 109 is configured to pivot about the living hinge and extend into the interior cavity of casing 10 only to the extent required for pin-like structures 70, which may be formed as integral to or part of the bottom surface or plate 109, to puncture cover 60 covering dry-powder compartment 19. However, it is contemplated that plate 109 of living hinge assembly 106 may have any length relative to the length of casing 10. For example, in one embodiment, plate 109 of living hinge assembly 106 may have a length that spans the majority of the length of casing 10.

In certain embodiments, the connected edge of plate 109 (e.g., the hinge in one embodiment or, e.g., attachment flange 89 in another embodiment) of living hinge assembly 106 may be located proximal to mouthpiece 12, such that the angle extending from the vertex of the living hinge opens in a direction facing air inlet 14. In other embodiments, the connected edge of plate 109 (e.g., the hinge in one embodiment or, e.g., attachment flange 89 in another embodiment) of living hinge assembly 106 may be located proximal to air inlet 14, such that the angle extending from the vertex of the living hinge opens in a direction facing mouthpiece 12. Other configurations are also possible, such as one in which the connected edge of plate 109 (e.g., the hinge in one embodiment or, e.g., attachment flange 89 in another embodiment) of living hinge assembly 106 is located on a side of plate 109, such that the angle extending from the vertex of the living hinge opens in a direction orthogonal to air inlet 14 and mouthpiece 12.

In certain embodiments, the inhalation device of the present invention may have one or more living hinge assemblies 106. In one embodiment, such as the embodiment illustrated in FIGS. 15*a* and 15*b*, the inhalation device includes two living hinges assemblies 106, one on the upper side of casing 10 and one on the lower side of casing 10.

In certain embodiments, living hinge assembly 106 may include a top, external surface of plate 109 and a bottom, internal surface of plate 109 relative to the internal cavity of casing 10. In some embodiments, a projection (or obstruction) 107 may be located on the top, external surface of plate 109, and at least one region of needle- or pin-like structures 70 may be located on the top or bottom, internal surface of plate 109. As discussed previously, the at least one region of pin-like structures 70 may be located on the bottom surface of plate 109 of living hinge assembly 106 so as to be in alignment with dry-powder compartment 19.

In certain embodiments, pin-like structures 70 may be formed from the bottom surface of plate 109 of living hinge assembly 106. In this embodiment, pin-like structures 70 may formed at the same time as casing 10 is manufactured, for example, when casing 10 is formed from a plastic mold, pin-like structures 70 may formed as part of the casing 10 mold.

In this regard, as shown in FIGS. 21*a* and 21*b*, bottom surface of plate 109 may include a projection that extends therefrom. FIG. 21*a* shows a projection that includes a region of pin-like structures 70, and FIG. 21*b* shows a projection that includes a blunt end support 72. In some embodiments, the projections on the bottom surface of plate 109 may extend at an angle relative to plate 109, and, as such, the pin-like structures 70 may also extend at an angle (see, e.g., FIG. 21*a*). The angle at which the projection with the pin-like structures extends relative to plate 109 ensures that the pin-like structures 70 (and the support 72 in FIG. 21*b*) strike the support panel 16 accurately and directly, such that the cover on compartment 19 is sufficiently punctured so as to cause the release of the medicament contained therein.

In certain embodiments, projection 107 may serve as the point of contact at which the user grasps the inhalation device and operates the device by pushing down on projection 107, thereby extending the at least one region of pin-like structures 70 towards dry-powder compartment 19 such that the structures 70 puncture cover 60 covering dry-powder compartment 19. As illustrated in FIGS. 15*a* and 15*b*, projection 107 may have a half spherical (e.g., hemispherical) or dome-like shape, although it is contemplated that projection 107 may have any desired shape such as a curved shape having a curved surface, or a triangular shape having a slanted face, facing in a direction towards or away from mouthpiece 12, as illustrated in FIG. 14. As discussed hereinbelow, puncture mechanism 200, which, in some embodiments, may be a leaf-spring assembly 104 or living hinge assembly 106 that is covered by cover 110 or projection 107, may be actuated to extend the at least one region of needle- or pin-like structures 70 into the interior cavity of casing 10 after the puncture mechanism 200 (e.g., the cover 110 or the projection 107) is struck or pressed by an obstruction upon the inhaler device being pulled from a compartment (e.g., a slot) of an inhaler kit.

In preferred embodiments, the hinge of living hinge assembly 106 is sufficiently flexible to allow the cut-out plate 109 to extend into the internal cavity of casing 10 upon exertion of pressure on projection 107, and to retract from the internal cavity once pressure on projection 107 has been removed. In a resting position, plate 109 of living hinge assembly 106 should not extend into the internal cavity of casing 10.

It is also contemplated, however, that a user may press and maintain pressure on the at least one push button 100 or puncture mechanism 200 while using the inhalation device. If a user maintains pressure on the at least one push button 100 or puncture mechanism 200 while using the device (e.g., inhaling), then the needle- or pin-like structures 70 remain exposed during inspiration, thereby creating a similar problem as discussed above where the constant exposure of the needle- or pin-like structures 70 may hinder the operation of the inhalation device. Accordingly, in certain embodiments of the present invention, it is desirable that user interaction with the at least one push button 100 or puncture mechanism 200 be kept to a minimum such that the user is prevented from maintaining pressure on the at least one push button 100 or puncture mechanism 200. In certain other embodiments, the user is not required to interact with the at least one push button 100 or puncture mechanism 200 and the at least one push button or puncture mechanism is actuated by other means in order to puncture the cover 60 of the drug compartment 19.

Figure 16:
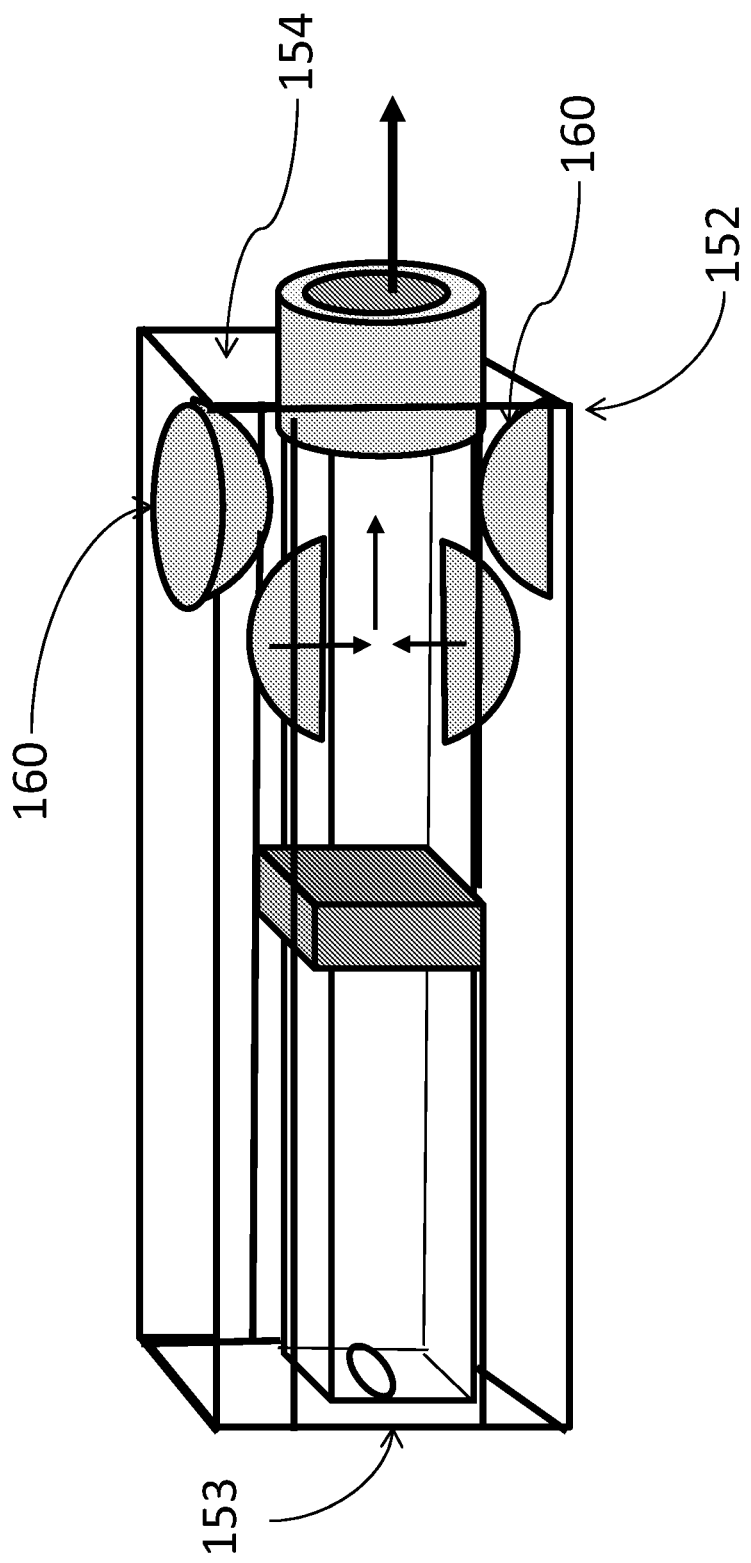
FIG. 16 shows a dispenser for dispensing a dry-powder inhaler device according to certain embodiments of the present invention.

Reference is now made to FIG. 16, which illustrates a dispenser 152 for dispensing one or more dry-powder inhaler devices according to certain embodiments of the present invention. Dispenser 151 may be in the form of a box or other container, or a sleeve, having an elongated compartment configured to hold a dry-powder inhalation device. Each dispenser 152 is preferably configured as a single-use dispenser that, as discussed hereinbelow, allows actuation of a dry-powder inhaler device contained therein for immediate use by a user.

Figure 23:
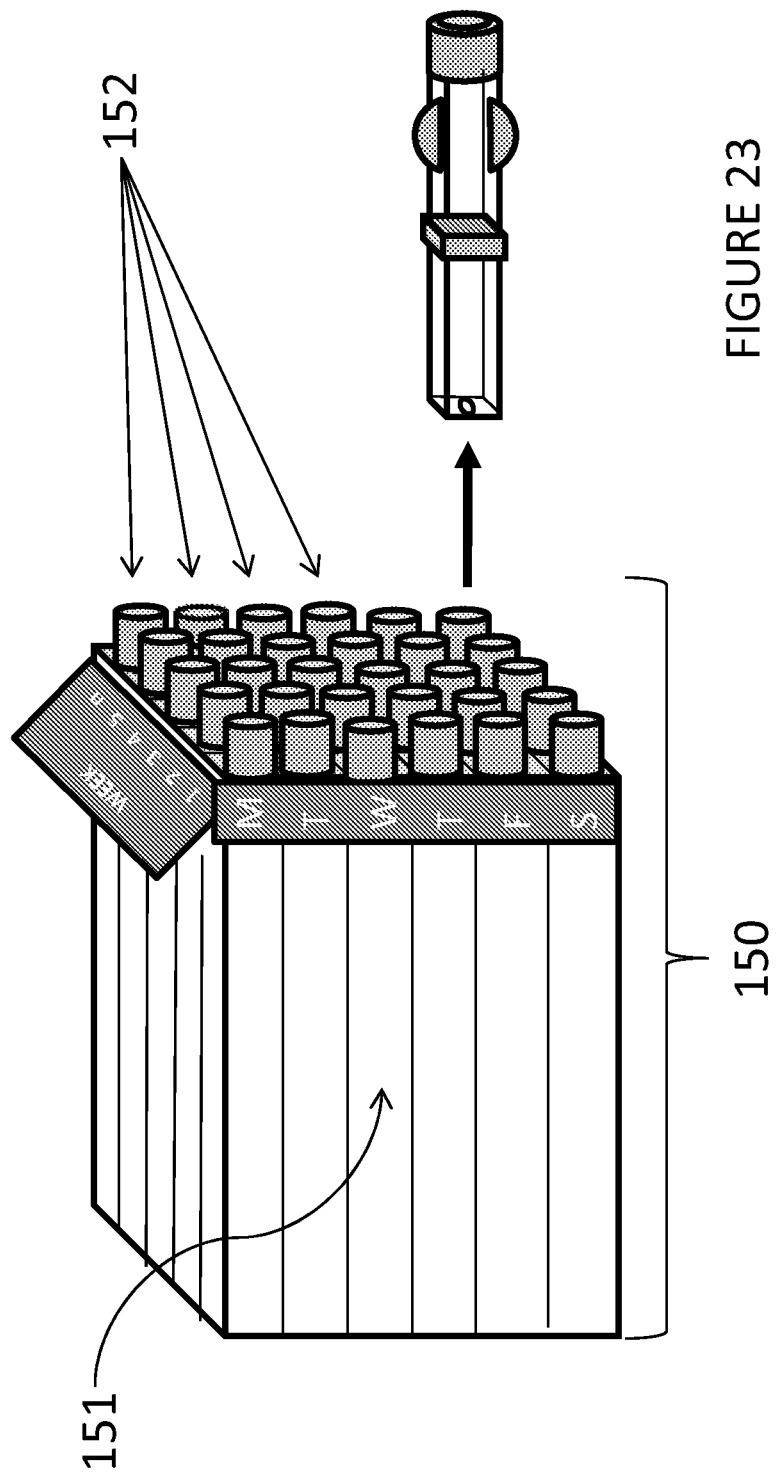
FIG. 23 shows a kit having a plurality of slots for dispensing one or more dry-powder inhaler devices according to aspects of certain embodiments of the present invention.

Reference is also made to FIG. 23, which illustrates a kit 150 for dispensing one or more dry-powder inhaler devices according to certain embodiments of the present invention. Kit 150 may comprise a container (e.g., a box or other configuration) having a plurality of elongated dispensing compartments or slots, each configured, like dispenser 152, to hold one dry-powder inhalation device. Dispenser 151 may include any number of dispensing slots 152 such as, for example, one slot (e.g., a single use kit), two slots, or more than two (e.g., a plurality) slots. In certain embodiments, dispenser 151 of kit 150 includes a dispensing slot 152 for each day of the month and is, therefore, configured to hold a month's supply of dry-powder inhalers. In other embodiments, dispenser 151 may include a dispensing slot 152 for each day of the week and is, therefore, configured to hold a week's supply of dry-powder inhalers. Other configurations are also possible.

The discussion below generally relates to a single-use dispenser 152 configured for actuation of a dry-powder inhaler device contained therein for immediate use by a user. However, it should be understood that this discussion may also relate to dispensing slots 152 within kit 150.

In preferred embodiments, dispenser 152 includes a closed back end 153 opposing an open dispenser opening 154 and is configured to hold a single dry-powder inhaler device, such as a dry-powder inhaler device according to certain embodiments of the present invention as described herein. It is contemplated that each dispenser 152 may hold at least one dry-powder inhaler device and, in some embodiments, more than one dry-powder inhaler device.

According to certain embodiments of the present invention, any embodiment of the dry-powder inhalation device as described herein may be placed in dispenser 152. In certain embodiments, the dry-powder inhaler rests within dispenser 152 with air inlet 14 located proximal to back end 153 and with mouthpiece 12 located proximal to dispenser opening 154. In some embodiments, mouthpiece 12 projects, or extends, out of dispenser opening 154 such as shown in, for example, FIG. 16, and provides a portion of the inhalation device that a user may grasp and pull in order to extract the inhalation device from dispenser 152. However, it is contemplated that, in other embodiments, mouthpiece 12 may not extend out from dispenser opening 154.

In certain embodiments, dispenser 152 includes at least one internal obstruction 160 extending into the internal volume of dispenser 152 and located, in certain embodiments, adjacent to a dispenser opening 154. In some embodiments, internal obstruction 160 may be located on a top, internal surface of dispenser 152, while in other embodiments internal obstruction 160 may be located on a bottom internal surface of dispenser 152. In some embodiments, dispenser 152 may include two internal obstructions 160 such as shown in, for example, FIG. 16. In the latter embodiment, a first internal obstruction 160 may be located on a bottom internal surface of dispenser 152, and a second internal obstruction 160 may be located on a top internal surface of dispenser 152. In preferred embodiments, obstruction(s) 160 are located proximal to dispenser opening 154, although other configurations are contemplated.

In preferred embodiments, the dry-powder inhalation device that is placed in dispenser 152 may include at least one cover 110 and/or at least one projection 107, each of which is associated with a puncture mechanism 200 that, when actuated, extends its pin-like structures 70 into the internal cavity of casing 10 to puncture cover 60 as discussed herein. The dry-powder inhalation device having projection 107 (which, as discussed herein, is associated in some embodiments with the living hinge assembly 106 of a puncture mechanism 200) is shown in FIG. 16 for clarity purposes only, since, as discussed above, puncture mechanism 200 may be formed as part of the plastic mold of casing 10, including hinges and leaf springs, as well as pin-like structures 70.

In preferred embodiments, the obstruction(s) 160 of dispenser 152 are positioned so as to be in operable alignment (e.g., a longitudinal alignment) with the projection(s) 107 of casing 10 and/or cover 110 on puncture mechanism 200 on the inhalation device. For example, the inhalation device may be arranged within dispenser 152 such that the inhalation device's projection(s) 107 and/or cover 110 are located behind (e.g., upstream from) obstruction 160 such as shown in, for example, FIG. 16. Obstruction 160 may have a half spherical (e.g., hemispherical) or dome-like shape, although it is contemplated that obstruction 160 may have any desired shape such as a curved shape having a curved or slanted face facing in a direction towards back end 153. In some embodiments, obstruction 160 may be a rod that is inserted horizontally through dispenser 152 in a direction that is orthogonal to a longitudinal axis of dispenser 152 as shown, for example, in FIGS. 17a, 17b, 20a and 20b. In any event, obstruction 160 should have a shape that is complementary to the shape of projection(s) 107 of casing 10 and/or cover 110 on puncture mechanism 200.

In this way, as the dry-powder inhalation device is withdrawn from dispenser 152, the casing's projection(s) 107 and/or cover 110 is pressed against obstruction(s) 160. Due to the rounded, curved or slanted complementary surfaces of each of projection 107 and obstruction 160, as well as the flexibility of puncture mechanism 200 (e.g., living hinge assembly 106 associated with projection 107), obstruction 160 actuates puncture mechanism 200 to extend the pin-like structures 70 into the internal cavity of casing 10, thereby puncturing cover 60 covering dry-powder compartment 19. As a result, the inhalation device is ready for use immediately after being removed from dispenser 152, thereby eliminating the need for the user to actuate a push button 100 or puncture mechanism 200.

In order to prevent actuation of puncture mechanism 200 during insertion of the dry-powder inhalation device into dispenser 152, it is contemplated that the dry-powder inhalation device would be inserted into dispenser 152 through back end 153 (which is first open and is subsequently closed in order to prevent the device from falling out). Alternatively, obstruction(s) 160 may be added to dispenser 152 after the inhalation device has been inserted (e.g., obstruction rods are inserted through corresponding channels adjacent to dispenser opening 154 after the dispenser 152 has been loaded with a dry-powder inhaler device).

Reference is now made to FIGS. 17a and 17b, which show perspective views of a dry-powder inhaler device having puncture mechanism 200 with a leaf-spring mechanism 104 packaged in a dispenser 152 according to aspects of certain embodiments of the present invention. FIG. 17a shows a dry-powder inhalation device fully installed within dispenser 152 and the puncture mechanism, leaf-spring mechanism 200/104 in a fully undepressed state, and FIG. 17b shows the dry-powder inhalation device as it is being pulled from dispenser 152 with puncture mechanism, leaf-spring mechanism 200/104 in a depressed configuration, and the pin-like structures extended into an interior of casing 10 to puncture cover 60 of compartment 19.

In the embodiment depicted in FIGS. 17a and 17b, dispenser 152 includes four internal obstructions 160, two towards back end 153, and two towards dispenser opening 154, but it is contemplated that, in certain embodiments, dispenser 152 may include one, two, three, or more than four internal obstructions 160. As discussed herein, it is contemplated that obstructions 160 may have any desired shape such as a curved shape or a triangular shape having a slanted surface, or obstruction 160 may be a rod that extends horizontally through dispenser 152 in a direction that is orthogonal to the slot's longitudinal axis (see, e.g., FIGS. 17a and 17b and FIGS. 20a and 20b).

In certain embodiments, the two obstructions 160 that are proximal to back end 153 as well as the two obstructions 160 that are proximal to dispenser opening 154 may be configured to hold the dry-powder inhalation device in an installed position (see, e.g., FIGS. 17a and 20a, which each show a dry-powder inhaler device positioned between the two back end obstructions and between the two front end obstructions such that the obstructions are configured to hold the inhaler device in place in an installed position). In preferred embodiments, as the dry-powder inhalation device is withdrawn from dispenser 152, the top panel 102 of the leaf-spring assembly 104 (or projection 107 of the living hinge assembly) is pressed against obstruction(s) 160. Due to the rounded, curved or slanted complementary surface of each projection 102,107 (or cover 110) or obstruction 160, as well as the flexibility of puncture mechanism, leaf-spring assembly 200/104 (or puncture mechanism, living hinge assembly 200/106), obstruction 160 actuates puncture mechanism 200 to extend the pin-like structures 70 into the internal cavity of casing 10, thereby puncturing cover 60 covering dry-powder compartment 19.

Reference is now made to FIGS. 18a and 18b, which show side views of a puncture mechanism, leaf-spring assembly 200/104 according to certain embodiments of the present invention. FIG. 18a shows a puncture mechanism, leaf-spring assembly 200/104*a* having a top panel 102, a projection including pin-like structures 70, and two flanges 88*a* and 88*b*. FIG. 18*b* shows a puncture mechanism, leaf-spring assembly 200/104*b* having a top panel 102, two flanges 88*a* and 88*b*, and a support 72. As shown in FIGS. 17*a* and 17*b*, the puncture mechanism, leaf-spring assemblies 200/104*a* and 200/104*b* are mounted on the dry-powder inhalation device such that they oppose each other as discussed elsewhere herein. In certain embodiments flanges 88*a* and 88*b* are configured to lock the puncture mechanism, leaf-spring assembly 200/104 into locks 86*a* and 86*b*, respectively, located on the casing's front housing 84 shown in, for example, FIG. 19 (see, also, FIGS. 17*a* and 17*b*). In certain embodiments, lock 86 may be a groove configured to accept a flange 88, although other ways of securely attaching puncture mechanism, leaf-spring assembly 200/104 to casing 10 is also contemplated.

FIGS. 18*a* and 18*b* each shows an elongated projection extending from a bottom surface of top panel 102. As shown in FIG. 18*a*, the elongated projection includes a region of pin-like structures 70. As shown in FIG. 18*b*, the elongated projection includes a blunt end (e.g., support 72). When the dry-powder inhalation device is withdrawn from dispenser 152, and obstructions 160 actuate puncture mechanism 200 as discussed elsewhere herein, the elongated projections of the two leaf-spring assemblies 104 are configured to extend through opening 103 of the casing's front housing 84 and into the interior of casing 10. In preferred embodiments, each elongated projection on the leaf-spring assemblies 104 has a length such that the pin-like structures 70 and support 72 are configured to strike support panel 16 at the same time, or close to the same time, which facilitates puncturing compartment 19 by pin-like structures 70 while support 72 supports the support panel 16 from underneath compartment 19.

In certain embodiments, casing 10 of the dry-powder inhalation device may be manufactured in two pieces such as, for example, a rear housing 82 and a front housing 84. FIG. 19 shows an exploded view of a two piece dry-powder inhaler device having a rear housing 82 and a front housing 84 according to certain aspects of the present invention. In some embodiments, a distal end of front housing 84 may be inserted into a proximal end of rear housing 82 such as depicted in, for example, FIGS. 17*a* and 17*b*, although other configurations are possible. Together, rear housing 82 and front housing 84 form casing 10, which includes the components of casing 10 discussed elsewhere herein.

FIGS. 20-22 show embodiments of the present invention similar to the embodiments discussed above with respect to FIGS. 17-19, although FIGS. 20-22 show embodiments of a dry-powder inhalation device having a puncture mechanism, living hinge assembly 200/106 according to aspects of the present invention.

Reference is now made to FIGS. 20*a* and 20*b*, which show perspective views of a dry-powder inhaler having a living hinge assembly 106 according to aspects of certain embodiments of the present invention. FIGS. 20*a* and 20*b* show a dry-powder inhalation device having a puncture mechanism, living hinge assembly 200/106 that is packaged in a dispenser 152 or dispensing slot 152 of a kit 150. FIG. 20*a* shows a dry-powder inhalation device fully installed within dispenser 152, while FIG. 20*b* shows the dry-powder inhalation device as it is being pulled from dispenser 152, wherein the pin-like structures are extended into an interior of casing 10 to puncture cover 60 of compartment 19.

In the embodiment depicted in FIGS. 20*a* and 20*b*, dispenser 152 includes four internal obstructions 160, two towards back end 153 and two towards dispenser opening 154, but it is contemplated that, in certain embodiments, dispenser 152 may include one, two, three or more than four internal obstructions 160. As discussed herein, it is contemplated that obstructions 160 may have any desired shape such as a curved shape, a triangular shape having a slanted surface, or obstruction 160 may be a rod that extends horizontally through dispenser 152 in a direction orthogonal to the slot's longitudinal axis (see also FIGS. 17*a* and 17*b*). In certain embodiments, the two obstructions 160 proximal to back end 153 in addition to the two obstructions 160 proximal to dispenser opening 154 may be configured to hold the dry-powder inhalation device in an installed position (see, e.g., FIGS. 17*a* and 20*a*, which each show a dry-powder inhaler device positioned between the two back end obstructions and between the two front end obstructions such that the obstructions are configured to hold the inhaler device in place in an installed position). In preferred embodiments, as the dry-powder inhalation device is withdrawn from dispenser 152, the projection 107 of the living hinge assembly 106 (or top panel 102 of the leaf-spring assembly 104) is pressed against obstruction(s) 160. Due to the rounded, curved or slanted surface of each projection 102,107 (or cover 110) and obstruction(s) 160, as well as the flexibility of puncture mechanism, living hinge assembly 200/106 (or puncture mechanism, leaf-spring assembly 200/104), obstruction(s) 160 actuates puncture mechanism 200 to extend the pin-like structures 70 into the internal cavity of casing 10, thereby puncturing cover 60 covering dry-powder compartment 19.

Reference is now made to FIGS. 21*a* and 21*b*, which show side views of a puncture mechanism, living hinge assembly 200/106 according to certain embodiments of the present invention. FIG. 21*a* shows a puncture mechanism, living hinge assembly 200/106*a* having a plate 109, a projection 107, a projection having pin-like structures 70, an attachment flange 89 and a curved flexible portion 87. FIG. 21*b* shows a puncture mechanism, living hinge assembly 200/106*b* having a plate 109, a projection 107, an attachment flange 89, a curved flexible portion 87, and a support 72.

As shown in use in FIGS. 20*a* and 20*b*, puncture mechanism, living hinge assemblies 200/106*a* and 200/106*b* are mounted on the dry-powder inhalation device such that they oppose each other as discussed elsewhere herein. In certain embodiments, attachment flange 89 is configured to lock the puncture mechanism, living hinge assembly 200/106 into lock 85 of the casing's front housing 84 shown in, for example, FIG. 22. In certain embodiments, lock 85 may be a groove configured to accept an attachment flange 89, although other ways of securely attaching puncture mechanism, living hinge assembly 200/106 to casing 10 are also contemplated.

FIGS. 21*a* and 21*b* each shows a projection extending from a bottom surface of plate 109. In FIG. 21*a*, the projection includes the region of pin-like structures 70. In FIG. 21*b*, the projection includes a blunt end (e.g., support 72). When the dry-powder inhalation device is withdrawn from dispenser 152 and obstructions 160 actuate puncture mechanism(s) 200 as discussed elsewhere herein, plate 109 along with the projections of the two living hinge assemblies 106 are configured to extend through opening 103 of front housing 84 and into the interior of casing 10. In preferred embodiments, each plate 109 and projection has a length such that the pin-like structures 70 and support 72 are configured to strike support panel 16 at or about the same time, which facilitates puncturing compartment 19 by pin-like structures 70, while support 72 supports the support panel 16 from underneath compartment 19.

In certain embodiments, the casing 10 of the dry-powder inhalation device may be manufactured in two pieces such as, for example, a rear housing 82 and a front housing 84. FIG. 22 shows an exploded view of a two-piece dry-powder inhaler device having a rear housing 82 and a front housing 84 according to certain aspects of the present invention. In some embodiments, a distal end of front housing 84 may be inserted into a proximal end of rear housing 82 such as depicted in, for example, FIGS. 20*a* and 20*b*, although other configurations are possible. Together, rear housing 82 and front housing 84 form casing 10, which includes the components of casing 10 discussed elsewhere herein.

Certain embodiments of the present invention may include a method of administering an inhalable therapeutic agent to a subject comprising the steps of providing a therapeutic agent inhaler device including a casing having an air inlet, a delivery port opposing the air inlet, an elongated support panel located within an interior cavity of the casing and having at least one covered compartment containing the therapeutic agent, and at least one push button or puncture mechanism comprising at least one needle structure, and puncturing the covered compartment with the at least one needle structure by operating (e.g., pressing and/or compressing) the at least one push button or puncture mechanism to extend the at least one needle into the interior of the casing and through the cover of the at least one compartment, whereby drawing air through the casing causes the elongated support panel to partially rotate about a single axis within the casing thereby releasing the therapeutic agent into the air flowing through the casing.

The method according to this embodiment of the present invention may further include releasing the at least one push button or puncture mechanism thereby retracting the at least one needle from the interior of the casing. The covered compartment may be located near the air inlet or near the drug delivery port, although the covered compartment is always in alignment with the at least one needle to allow puncturing of the covered compartment. Accordingly, the push button or puncture mechanism (which in preferred embodiments includes the at least one needle) is typically located in operable alignment with the covered compartment, although alternative embodiments are contemplated. In certain embodiments, and as discussed above, the single axis may be located on the elongated support panel at an approximate mid-point (e.g., center), at a position near the air inlet, or at a position near the drug delivery port. In certain embodiments, the at least one needle is a region comprising a plurality of needles.

As discussed above, the airflow through the device causes the support panel 16 to repeatedly rotate between the two states. In some embodiments, each time this occurs, the support panel end 24, comprising the needle- or pin-like structures 70 distal or proximal to the air inlet 14, beats against an internal surface 26 of the casing 10 containing the dry-powder containing compartment 19, causing the dry-powder compartment 19 to be punctured or ruptured by the needle- or pin-like structures 70 aligned with the cover 60, thereby causing the dry-powder drug within the compartment 19 to be released gradually from compartment 19.

In other embodiments, a user may apply a force to a push button 100 or puncture mechanism 200 to extend the needle-like structures 70 into the internal cavity of casing 10, thereby puncturing the cover 60 of compartment 19, and, thereafter, airflow through the device causes the support panel 16 to repeatedly rotate between the two states, thereby causing the dry-powder drug within punctured compartment 19 to be released gradually from compartment 19. After the user ceases the force on push button 100 or puncture mechanism 200, the push button 100 or puncture mechanism 200 is configured to rebound, thereby retracting the needle-like structures 70 from the internal cavity of casing 10.

In yet other embodiments, a user may pull a dry-powder inhalation device from a dispenser 152 or from a dispensing slot 152 of a kit 150 having an obstruction 160 located adjacent to a dispenser opening 154, wherein, as the device is pulled from the dispenser and push button 100 or puncture mechanism 200 is pulled past obstruction 160, obstruction 160 applies a force to push button 100 or puncture mechanism 200 to thereby extend the needle-like structures 70 into the internal cavity of casing 10, thereby puncturing the cover 60 of compartment 19. Thereafter, airflow through the device causes the support panel 16 to repeatedly rotate between the two states, thereby causing the dry-powder drug within punctured compartment 19 to be released gradually from compartment 19. After the push button 100 or puncture mechanism 200 has passed obstruction 160, the force on push button 100 or puncture mechanism 200 is released, and push button 100 or puncture mechanism 200 is configured to rebound, thereby retracting the needle-like structures 70 from the internal cavity of casing 10.

Certain embodiments of the present invention may also include a method of dispensing a dry-powder inhalation device comprising the steps of providing a dispenser having at least one compartment configured to hold a dry-powder inhalation device, each compartment comprising at least one obstruction configured to strike a corresponding projection located on the dry-powder inhalation device as the inhalation device is removed from the compartment, and removing the dry-powder inhalation device, thereby activating the dry-powder inhalation device for use.

Certain embodiments of the present invention may also include a method of dispensing a dry-powder inhalation device comprising the steps of providing a kit having at least one dispensing slot configured to hold a dry-powder inhalation device, each dispensing slot comprising at least one obstruction configured to strike a corresponding projection located on the dry-powder inhalation device as the inhalation device is removed from the dispensing slot, and removing the dry-powder inhalation device, thereby activating the dry-powder inhalation device for use.

Other embodiments of the present invention may include a method for activating and dispensing one or more dry-powder inhaler devices, the method including the steps of providing a dispenser configured to hold at least one dry-powder inhaler device, the at least one dry-powder inhaler device including a casing enclosing at least one compartment containing an inhalable medicament covered by a cover, and at least one puncture mechanism including at least one pin structure operably aligned with the at least one compartment, the at least one dispenser including at least one obstruction internally located within the dispenser adjacent to an opening, and activating the at least one dry-powder inhaler device by pulling the at least one dry-powder inhaler device from the dispenser, causing the at least one obstruction to actuate the at least one puncture mechanism, thereby extending the at least one pin structure into the casing puncturing the cover of the at least one compartment.

Other embodiments of the present invention may include a method for activating and dispensing one or more dry-powder inhaler devices, the method including the steps of providing a kit having at least one dispensing slot configured to hold at least one dry-powder inhaler device, the at least one dry-powder inhaler device including a casing enclosing at least one compartment containing an inhalable medicament covered by a cover, and at least one puncture mechanism including at least one pin structure operably aligned with the at least one compartment, the at least one dispensing slot including at least one obstruction internally located within the dispensing slot adjacent to an opening, and activating the at least one dry-powder inhaler device by pulling the at least one dry-powder inhaler device from the at least one dispensing slot, causing the at least one obstruction to actuate the at least one puncture mechanism, thereby extending the at least one pin structure into the casing puncturing the cover of the at least one compartment.

The inhalers, kits and/or methods of the present invention, inter alia, are well suited to deliver two or more inhaled dry-powder drugs simultaneously while storing them separately.

From a chemical perspective, the co-storage of two or more drugs within the same physical compartment can be problematic as the two drugs may interact, especially if they have different pHs. From a regulatory standpoint, it may be necessary to prove that there is no such interaction over a long time period, and this can add significant expense to the regulatory approvals process.

In some embodiments, according this aspect of the invention, a technical challenge in the inhaler industry involving the storage of two or more drugs, which is potentially problematic for both chemical and regulatory reasons, is obviated by certain embodiments of this invention.

The assemblies of this invention may comprise, in some embodiments, one or more compartments, with each compartment comprising a dry-powder. In some embodiments, when the assemblies comprise more than one compartment, each compartment may comprise the same or different dry-powders.

In some embodiments, the support panel comprises two or three compartments containing a dry-powder. According to this aspect of the invention, and in some embodiments, the two or three compartments comprise two or three different dry-powders.

In some embodiments, the support panel comprises a compartment containing at least one or two partitions, which partitions create separate chambers in the compartment. According to this aspect of the invention, and in some embodiments, the separate chambers may contain different dry-powders.

In some embodiments, when the support panel 16 comprises two or more chambers or compartments 19, the support panel 16 may strike the protruding surface at a region between the two chambers or compartments 19, or in some embodiments, the interior surface may comprise multiple protruding surfaces such that each chamber or compartment will strike the interior surface at a region containing a protruding surface.

For example, in certain embodiments, each compartment 19 on support panel 16 is aligned with a corresponding region of needle-like structures 70, or comb of needle-like structures 70.

In some embodiments, the present invention provides for a method of dispensing dry-powder from an inhaler, comprising facilitating airflow through a dry-powder inhaler device including any single or combined embodiments described herein, to cause the support panel to partially rotate within the casing about a single axis causing the covered compartment 19 to strike one or more needle- or pin-like structures 70, thereby puncturing the cover 60, releasing dry-powder from the compartment 19 to become entrained in the airflow, and dispensing dry-powder from the inhaler. FIG. 2 depicts an embodiment whereby a principle mode of operation of an embodied device of this invention results in the dispensing of a dry-powder from an inhaler of this invention, which represents an aspect of the methods of this invention.

In certain embodiments, the inhaler devices of this invention may be single use devices, which are preloaded with a desired dry-powder agent, at a desired dosage.

In some embodiments, according to this aspect, care is taken to ensure appropriate dry-powder containment within the blistered compartments of the inhaler devices of the present invention, prior to or between uses of the inhaler device.

It will be evident to those skilled in the art that the invention is not limited to the details of the foregoing illustrative embodiments and that the present invention may be embodied in other specific forms without departing from the spirit or essential attributes thereof.

The embodiments presented herein are, therefore, to be considered in all respects as illustrative and not restrictive of the scope of the invention, and the skilled artisan will appreciate the appropriate equivalents thereto, which are to be considered as part of this invention.

The invention claimed is:

1. A dispenser for dispensing at least one dry-powder inhaler device, the at least one dry-powder inhaler device comprising a casing enclosing at least one medicament compartment containing an inhalable medicament covered by a cover and at least one puncture mechanism comprising at least one pin structure operably aligned with the at least one medicament compartment, the dispenser comprising:

a dispensing compartment configured to hold at least one dry-powder inhaler device, and at least one obstruction internally located within the dispensing compartment and adjacent to an opening in the dispensing compartment, wherein, the at least one dry-powder inhaler device is pulled from the dispensing compartment, the at least one obstruction is configured to actuate the at least one puncture mechanism to cause the at least one pin structure to extend into the casing, thereby puncturing the cover of the at least one medicament compartment.

2. The dispenser according to claim 1, wherein the puncture mechanism comprises a spring mechanism.

3. The dispenser according to claim 2, wherein the spring mechanism is a leaf-spring assembly.

4. The dispenser according to claim 3, wherein the leaf-spring assembly comprises a top panel, a projection configured to hold the at least one pin structure, and at least two flanges configured to attach the leaf-spring assembly to the casing, wherein pulling the at least one dry-powder inhaler device from the slot causes the obstruction to strike the top panel, which in turn presses the projection, thereby causing the leaf-spring assembly to extend the least one pin structure into the casing.

5. The dispenser according to claim 1, wherein the puncture mechanism comprises a living hinge assembly.

6. The dispenser according to claim 5, wherein the living hinge assembly is formed integral with the casing, the living hinge assembly comprising:

a plate having an edge attached to the casing, a first plate surface having a projection extending therefrom, and a second plate surface configured to hold the at least one pin structure, wherein pulling the at least one dry-powder inhaler device from the compartment causes the obstruction to strike and press the projection, thereby causing the living hinge assembly to extend the least one pin structure into the casing.

7. The dispenser according to claim 5, wherein the living hinge assembly comprises:
   a plate having a first plate surface having a projection extending therefrom and a second plate surface configured to hold the at least one pin structure,
   an attachment flange configured to attach the plate to the casing;
   a curved flexible portion joining the attachment flange to the plate and configured to flex upon actuation of the living hinge assembly;
   wherein pulling the at least one dry-powder inhaler device from the slot causes the obstruction to strike and press the projection, thereby causing the living hinge assembly to extend the least one pin structure into the casing.

8. The dispenser according to claim 1, wherein the at least one dry-powder inhaler device further comprises:
   an air inlet located at a first terminus of the casing;
   a powder delivery port located at a second terminus of the casing and positioned distal to the air inlet; and
   an elongated support panel comprising a first terminus and a second terminus at opposite ends thereof, the at least one compartment containing the inhalable medicament located proximal to the first terminus;
   the support panel being rotatably mounted within an interior of the casing such that the first terminus is located proximal to the air inlet, the second terminus is located proximal to the powder delivery port, and the support panel partially rotates within the casing about a single axis upon flowing of air through the casing;
   wherein, after the at least one puncture mechanism punctures the cover of the at least one compartment, and upon partial rotation of the elongated support panel within the casing, the punctured cover is adapted to allow the medicament contained within the at least one compartment to become released into air flowing through the device.

9. A kit for dispensing one or more dry-powder inhaler devices, the kit comprising:
   a container comprising a plurality of dispensers according to claim 1.

10. A method for activating a dry-powder inhaler device, the method comprising:
    providing a dispenser having
       at least one dispenser compartment configured to hold at least one dry-powder inhaler device, the at least one dry-powder inhaler device comprising a casing enclosing at least one medicament compartment containing an inhalable medicament covered by a cover, and at least one puncture mechanism comprising at least one pin structure operably aligned with the at least one medicament compartment,
       the at least one dispenser compartment comprising at least one obstruction internally located within the slot adjacent to a dispenser compartment opening; and
    arranging the at least one dry-powder inhaler device in the at least one dispenser compartment such that, when the at least one dry-powder inhaler device is pulled from the at least one dispenser compartment, the at least one obstruction actuates the at least one puncture mechanism, thereby causing the at least one pin structure to extend into the casing, thereby puncturing the cover of the at least one medicament compartment.

11. The method according to claim 10, wherein the puncture mechanism comprises a spring mechanism or a living hinge assembly.

12. The method according to claim 11,
    wherein the spring mechanism is a leaf-spring assembly, the leaf-spring assembly comprising a top panel, a projection configured to hold the at least one pin structure, and at least two flanges configured to attach the leaf-spring assembly to the casing,
    wherein the at least one dispenser compartment is configured such that, when the at least one dry-powder inhaler device is pulled from the at least one dispenser compartment, the at least one obstruction strikes and presses the top panel, thereby causing the at least one pin structure to extend into the casing.

13. The method according to claim 11, wherein the living hinge assembly is formed integral with the casing, the living hinge assembly comprising:
    a plate having an edge attached to the casing, a first plate surface having a projection extending therefrom, and a second plate surface configured to hold the at least one pin structure;
    wherein the at least one dispenser compartment is configured such that, when the at least one dry-powder inhaler device is pulled from the at least one dispenser compartment, the at least one obstruction strikes and presses the projection, thereby causing the at least one pin structure to extend into the casing.

14. The method according to claim 11, wherein the living hinge assembly comprises:
    a plate having a first plate surface having a projection extending therefrom and a second plate surface configured to hold the at least one pin structure,
    an attachment flange configured to attach the plate to the casing;
    a curved flexible portion joining the attachment flange to the plate and configured to flex upon actuation of the living hinge assembly;
    wherein the at least one dispenser compartment is configured such that, when the at least one dry-powder inhaler device is pulled from the at least one dispenser compartment, the at least one obstruction strikes and presses the projection, thereby causing the at least one pin structure to extend into the casing.

15. An inhaler device comprising:
    a casing having at least one puncture mechanism located on an external portion thereof, the puncture mechanism comprising at least one pin structure, wherein the puncture mechanism comprises a leaf-spring assembly or a living hinge assembly;
    an air inlet located at a first terminus of the casing;
    a powder delivery port located at a second terminus of the casing and positioned distal to the air inlet; and
    an elongated support panel comprising a first terminus and a second terminus at opposite ends thereof and at least one compartment containing an inhalable medicament located proximal to the first terminus and covered by a cover that is configured to be punctured by the at least one pin structure,
    the support panel being rotatably mounted within an interior of the casing such that the first terminus is located proximal to the air inlet, the second terminus is located proximal to the powder delivery port, and the support panel partially rotates within the casing about a single axis upon flowing of air through the casing;

wherein the puncture mechanism has a depressed state and an undepressed state and, upon application of a force, the at least one puncture mechanism is configured to transition to the depressed state causing the at least one pin structure to extend into the casing and puncture the cover of the at least one compartment, wherein, upon partial rotation of the elongated support panel within the casing, the punctured cover is adapted to allow the medicament contained within the at least one compartment to become released into air flowing through the device.

16. The inhaler device according to claim 15, wherein the leaf-spring assembly comprises a top panel, a projection configured to hold the at least one pin structure, and at least two flanges configured to attach the leaf-spring assembly to the casing, wherein application of the force on the top panel transitions the leaf-spring assembly to the depressed state, thereby causing the projection and at least one pin structure to extend into the casing and puncture the cover of the at least one compartment.

17. The inhaler device according to claim 15, wherein the living hinge assembly is formed integral with the casing, the living hinge assembly comprising:

a plate having an edge attached to the casing, a first plate surface having a projection extending therefrom, and a second plate surface configured to hold the at least one pin structure;

wherein application of the force on the projection transitions the living hinge assembly to the depressed state, thereby causing the plate and at least one pin structure to extend into the casing and puncture the cover of the at least one compartment.

18. The inhaler device according to claim 15, wherein the living hinge assembly comprises a plate comprising:

a plate having a first plate surface having a projection extending therefrom and a second plate surface configured to hold the at least one pin structure, an attachment flange configured to attach the plate to the casing;

a curved flexible portion joining the attachment flange to the plate and configured to flex upon actuation of the living hinge assembly;

wherein application of the force on the projection transitions the living hinge assembly to the depressed state, thereby causing the plate to flex about the curved flexible portion and extend the at least one pin structure into the casing and puncture the cover of the at least one compartment.

* * * * *